US012624387B2

(12) United States Patent
Lee et al.

(10) Patent No.: US 12,624,387 B2
(45) Date of Patent: May 12, 2026

(54) METHOD FOR REDUCING PRIMER DIMER FORMATION AND INCREASING AMPLIFICATION EFFICIENCY

(71) Applicant: SEEGENE, INC., Seoul (KR)

(72) Inventors: Young Jo Lee, Seoul (KR); Dae Young Kim, Seoul (KR)

(73) Assignee: SEEGENE, INC., Seoul (KR)

( * ) Notice: Subject to any disclaimer, the term of this patent is extended or adjusted under 35 U.S.C. 154(b) by 0 days.

(21) Appl. No.: 16/474,168

(22) PCT Filed: Dec. 22, 2017

(86) PCT No.: PCT/KR2017/015386
§ 371 (c)(1),
(2) Date: Jun. 27, 2019

(87) PCT Pub. No.: WO2018/124665
PCT Pub. Date: Jul. 5, 2018

(65) Prior Publication Data
US 2019/0316193 A1      Oct. 17, 2019

(30) Foreign Application Priority Data

Dec. 29, 2016    (KR) ........................ 10-2016-0182955

(51) Int. Cl.
*C12Q 1/68*          (2018.01)
*C12P 19/34*        (2006.01)
*C12Q 1/6853*      (2018.01)

(52) U.S. Cl.
CPC ............ *C12Q 1/6853* (2013.01); *C12P 19/34* (2013.01)

(58) Field of Classification Search
None
See application file for complete search history.

(56) References Cited

U.S. PATENT DOCUMENTS

| | | | | |
|---|---|---|---|---|
| 5,681,947 A | * | 10/1997 | Bergstrom ............. | C07H 19/24 536/26.9 |
| 7,169,557 B2 | | 1/2007 | Rosenblum et al. | |
| 8,182,996 B2 | | 5/2012 | Bergeron et al. | |
| 2003/0170711 A1 | | 9/2003 | Brown et al. | |
| 2007/0087341 A1 | * | 4/2007 | Sampath ................ | C12Q 1/701 435/5 |
| 2010/0240102 A1 | * | 9/2010 | Duncan ................ | C12Q 1/6846 435/91.2 |

| | | | | |
|---|---|---|---|---|
| 2012/0135473 A1 | | 5/2012 | Chun | |
| 2012/0164692 A1 | * | 6/2012 | Chun ................... | C12Q 1/6876 435/91.2 |
| 2012/0258447 A1 | * | 10/2012 | Chun ................... | C12Q 1/6851 435/6.12 |
| 2015/0086987 A1 | * | 3/2015 | Wolff ................... | C12Q 1/6895 536/24.32 |
| 2015/0225775 A1 | * | 8/2015 | Satya ................... | C12Q 1/686 435/6.12 |

FOREIGN PATENT DOCUMENTS

| | | | | |
|---|---|---|---|---|
| WO | WO-2011046972 A2 | * | 4/2011 | ........... C12Q 1/6848 |
| WO | WO-2013/081755 A1 | | 6/2013 | |

OTHER PUBLICATIONS

Christopherson et al. The effect of internal primer-target mismatches on RT-PCR: HIV-1 model studies. Nucleic Acids Research, vol. 25(3), p. 654-658 (Year: 1997).*

Verstraete K. et al. A qPCR assay to detect and quantify shiga toxin-producing *E. coli* (STEC) in cattle and on farms: A potential predictive tool for STEC culture-positive farms. Toxins, vol. 6, p. 1201-1221, (2014).*

Tahir et al. A modified strategy of multiplex RT-PCR for simultaneous detection of H5, H7, and H9 subtypes of avian influenza virus based on common forward oligo. Appl. Poult. Res., vol. 25, p. 322-327 (2016).*

Sugita et al. Use of multiplex and real-time PCR to detect herpes virus genome in ocular fluids of patients with uveitis. Br. J. Opthalmol., vol. 92, p. 928-932, (2008).*

Watkins et al. Nearest-neighbor thermodynamics of deoxyinosine pairs in DNA duplexes. Nucleic Acids Research, vol. 33(19), p. 6258-6267, (2005).*

Knoth, K., et al. Highly degenerate, inosine-containing primers specifically amplify rare cDNA using polymerase chain reaction. Nucleic Acids Research, vol. 16(22), p. 10932, (1988).*

International Search Report (ISR) from corresponding PCT Application No. PCT/KR2017/015386, mailed on Apr. 11, 2018.

Kilpatrick, D. et al., "Poliovirus serotype-specific VP1 sequencing primers", Journal of Virological Methods, 2011, vol. 174, No. 1, pp. 128-130.

* cited by examiner

*Primary Examiner* — Suryaprabha Chunduru

(74) *Attorney, Agent, or Firm* — Harness, Dickey & Pierce, P.L.C.

(57) ABSTRACT

The present invention relates to a method for amplifying at least three target nucleic acid molecules with reduced primer dimer formation in a multiplex amplification reaction. The method of present invention can inhibit primer dimer formation and hence generation of nonspecific amplification products in an effective manner in a multiplex amplification reaction for at least three target nucleic acid molecules.

15 Claims, 10 Drawing Sheets

Specification includes a Sequence Listing.

Dimer type

Non-extendable primer dimer

One-strand extendable primer dimer

Both-strands extendable primer dimer

Dimer amplification

UP target amplification

29 (Conventional)

29A (UBP)

29B (UBP)

29C (UBP)

29D (UBP)

29E (UBP)

29F (UBP)

29G (UBP)

NG target amplification

METHOD FOR REDUCING PRIMER DIMER FORMATION AND INCREASING AMPLIFICATION EFFICIENCY

CROSS-REFERENCE TO RELATED APPLICATIONS

This application is a national phase application of PCT Application No. PCT/KR2017/015386, filed on Dec. 22, 2017, which claims the benefit and priority to Korean Patent Application No. 10-2016-0182955, filed Dec. 29, 2016. The entire disclosures of the applications identified in this paragraph are incorporated herein by references.

FIELD OF THE INVENTION

The present invention relates to a method for reducing primer dimer formation and increasing amplification efficiency in multiplex amplification reactions.

BACKGROUND OF THE INVENTION

Nucleic acid amplification is a pivotal process for a wide variety of methods in molecular biology, such that various amplification methods have been proposed. For example, Miller, H. I. et al. (WO 89/06700) discloses a method for amplifying nucleic acids, comprising the hybridization of a promoter/primer sequence to a target single-stranded DNA ("ssDNA") followed by transcription of many RNA copies of the sequence. Other known nucleic acid amplification procedures include transcription-based amplification systems (Kwoh, D. et al., *Proc. Natl. Acad. Sci. U.S.A.*, 86:1173 (1989); and Gingeras T. R. et al., WO 88/10315).

The most predominant process for a nucleic acid amplification known as polymerase chain reaction (hereinafter referred to as "PCR") is based on repeated cycles of denaturation of double-stranded DNA, followed by oligonucleotide primer annealing to the DNA template, and primer extension by a DNA polymerase (Mullis et al. U.S. Pat. Nos. 4,683,195, 4,683,202, and 4,800,159; Saiki et al., (1985) *Science* 230, 1350-1354).

PCR-based techniques have been widely used not only for amplification of a target DNA sequence, but also for scientific applications or methods in the fields of biological and medical research, such as reverse transcriptase PCR (RT-PCR), differential display PCR (DD-PCR), cloning of known or unknown genes by PCR, rapid amplification of cDNA ends (RACE), arbitrary priming PCR (AP-PCR), multiplex PCR, SNP genome typing, and PCR-based genomic analysis (McPherson and Moller, (2000) PCR. BIOS Scientific Publishers, Springer-Verlag New York Berlin Heidelberg, NY).

Since the PCR-based techniques involve amplification of the target nucleic acid molecule, it is required to amplify only the target sequence accurately and efficiently. For this purpose, it is necessary to select primers of appropriate sequence and length and perform an amplification reaction by appropriately adjusting the type and content of the components used (e.g., DNA polymerase, dNTPs, Mg ions and buffers) and the reaction temperature/time. However, in some cases, it is difficult to select optimum reaction conditions, and satisfactory amplification efficiency may not be achieved even under the selected reaction conditions. Various methods have been developed for more efficient amplification.

Meanwhile, reduced amplification efficiency may be caused by the formation of primer dimers. In this regard, Lebedev et at discloses a method for improving the specificity and the amplification efficiency by using a primer in which 4-oxo-1-pentyl (OXP) phosphotriester (PTE) group is introduced at the 3' terminal phosphodiester linkage or at the penultimate phosphodiester linkage of the primer, to prevent the non-specific hybridization of the primers occurring under low temperature condition at an initial reaction (See Lebedev et al., Nucleic Acids Res 2008; 36: e131).

Primers have a significant effect on the specificity and efficiency of the amplification reaction, because they specifically hybridize to a target nucleic acid molecule and initiate its amplification. Particularly, the importance of primers is further emphasized in multiplex amplification reactions using multiple primers.

Typically, a method of altering the site where the primer is hybridized or adjusting the sequence or length of the primer has been used to minimize primer dimer formation; however, it has limitations in applying to the design of primers used in multiplex amplification reactions. Thus, there remains a need for a novel method for effectively inhibiting the primer dimer formation, and such method would improve the amplification efficiency in a more economical and convenient manner alone or in combination with known methods as described above.

Throughout this application, various patents and publications are referenced and citations are provided in parentheses. The disclosure of these patents and publications in their entirety are hereby incorporated by references into this application in order to more fully describe this invention and the state of the art to which this invention pertains.

SUMMARY OF THE INVENTION

The present inventors have endeavored to develop a method capable of effectively reducing the formation of the primer dimer in a multiplex amplification reaction, particularly for at least three target nucleic acid molecules. As a result, the present inventors have found that the use of a primer(s) containing a universal base nucleotide(s) in a multiplex amplification reaction can lead to inhibited primer dimer formation, thereby increasing amplification efficiency.

Accordingly, it is an object of the present invention to provide a method for amplifying at least three target nucleic acid molecules with reduced primer dimer formation.

It is another object of the present invention to provide a method for reducing primer dimer formation in a multiplex amplification reaction for at least three target nucleic acid molecules.

It is still another object of the present invention to provide a kit for amplifying at least three target nucleic acid molecules with reduced primer dimer formation in a multiplex amplification reaction.

It is further object of the present invention to provide a use of a kit for amplifying at least three target nucleic acid molecules with reduced primer dimer formation in a multiplex amplification reaction.

It is still further object of the present invention to provide a computer readable storage medium containing instructions to configure a processor to design primer pairs for use in a method for amplifying at least three target nucleic acid molecules with reduced primer dimer formation.

Other objects and advantages of the present invention will become apparent from the detailed description to follow taken in conjugation with the appended claims and drawings.

DETAILED DESCRIPTION OF THIS INVENTION

In a first aspect of this invention, there is provided a method for amplifying at least three target nucleic acid molecules with reduced primer dimer formation in a multiplex amplification reaction, comprising the steps of:

(a) preparing at least three primer pairs, each primer pair comprising a forward primer and a reverse primer; wherein each primer comprises a hybridizing nucleotide sequence to a corresponding target nucleic acid molecule; wherein either or both of primers in at least one primer pair are universal base primers (UBPs); wherein the UBP has 1-3 universal base nucleotides; wherein one or two of the universal base nucleotides are located in a core region ranging from $3^{rd}$ nucleotide to $6^{th}$ nucleotide at the 3'-end of the UBP, and the remainder is located in a region ranging from $4^{th}$ nucleotide at the 5'-end of the UBP to $7^{th}$ nucleotide at the 3'-end of the UBP such that a multiplex amplification reaction using the UBPs generates amplification products of the target nucleic acid molecules with reduced primer dimer formation; wherein the universal base nucleotides are nonconsecutive in the UBP; and (b) performing a multiplex amplification reaction comprising at least two cycles of primer annealing, primer extension and denaturation by using the at least three primer pairs; wherein the multiplex amplification reaction generates amplification products of the target nucleic acid molecules with reduced primer dimer formation.

The present inventors have endeavored to develop a method capable of effectively reducing the formation of the primer dimer in a multiplex amplification reaction, particularly for at least three target nucleic acid molecules. As a result, the present inventors have found that the use of a primer(s) containing a universal base nucleotide(s) in a multiplex amplification reaction can lead to inhibited primer dimer formation, thereby increasing amplification efficiency.

In a conventional nucleic acid amplification reaction, non-specific byproducts such as primer dimers may be inadvertently generated by inter-primer hybridization. The present invention pertains to inhibiting a primer dimer among non-specific byproducts.

The term "primer dimer" as used herein refers to a hybrid formed by inter-hybridization of two primers or by intra-hybridization (self-hybridization) of a single primer. In particular, the primer dimer includes a hybrid which is formed by a pair of primers that hybridize to same or different target nucleic acid molecules. Furthermore, the primer dimer as used herein includes not only a hybrid of two primers per se but also an extension product in which either or both primer strands constituting the hybrid are extended.

Depending on whether each primer strand of primer dimer is extended or not, primer dimers can be divided into three categories: (i) non-extendable primer dimer; (ii) one-strand extendable primer dimer; and (iii) both-strands extendable primer dimer (see FIG. 2).

Figure 1:
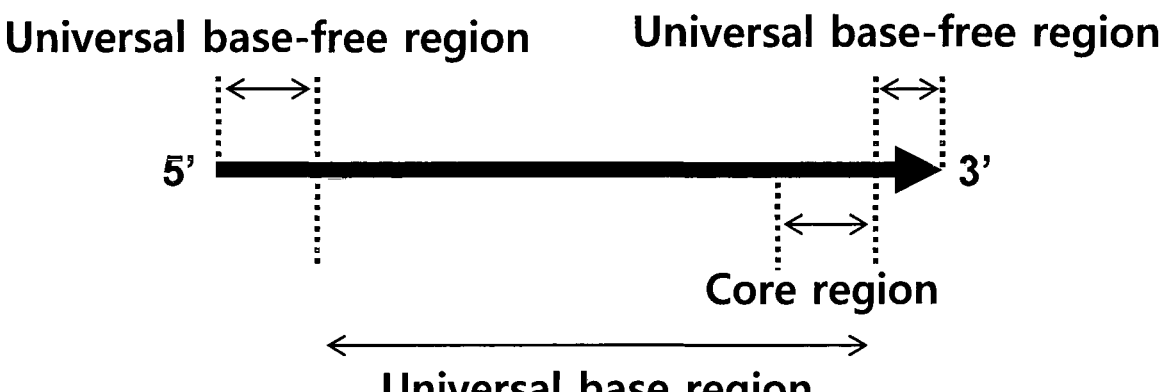
FIG. 1 shows the schematic structure of a universal base primer (UBP) according to the present invention. The UBP comprises two universal base-free regions at both ends and a universal base region comprising a core region.
Figure 2:
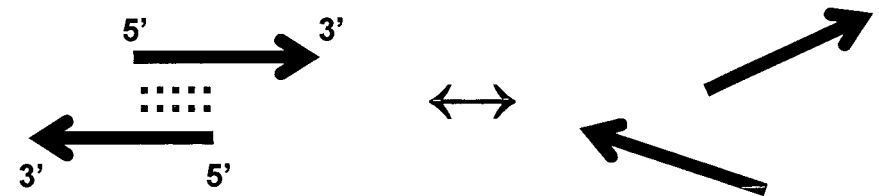
FIG. 2 shows three types of primer dimers that can be inadvertently generated in a multiplex amplification reaction: non-extendable primer dimer (top row); one-strand extendable primer dimer (middle row); and both-strands extendable primer dimer (bottom row).
Figure 2:
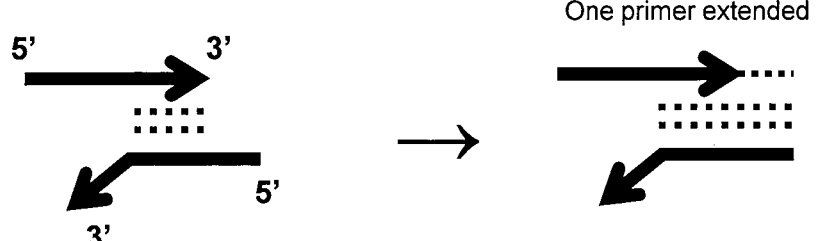
Figure 2:
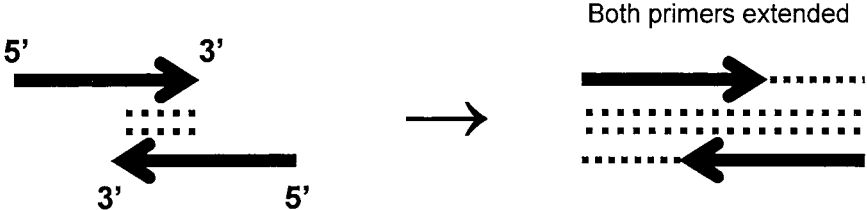

Non-extendable primer dimer as used herein refers to those in which both primer strands following hybridization are not extended by a nucleic acid polymerase (see the top row of FIG. 2). One-strand extendable primer dimer as used herein refers to those in which one of two primer strands following hybridization is extended by a nucleic acid polymerase (see the middle row of FIG. 2). Both-strands extendable primer dimer refers to those in which both primer strands following hybridization are extended by a nucleic acid polymerase (see the bottom row of FIG. 2).

According to our experiments, the formation of the non-extendable primer dimer or the one-strand extendable primer dimer has no significant influence on the amplification of the target nucleic acid molecule, whereas the formation of the both-strands extendable primer dimer hinders the primers from hybridizing to the target nucleic acid molecule in a nucleic acid amplification reaction. Also, the amplification of the both-strands extendable primer dimer may cause waste of enzymes, dNTPs, etc., to be used in the target nucleic acid amplification reaction and increase nonspecific amplification products that compete with the target nucleic acid molecule for binding to the primer, thereby eventually deteriorating the efficiency of the normal nucleic acid amplification reaction.

Accordingly, the present invention focuses on inhibiting undesired formation and amplification of both-strands extendable primer dimers to improve target amplification efficiency.

The steps of the method of the present invention will be described in detail as follows:

Step (a): Preparation of at Least Three Primer Pairs

According to the present invention, at least three target nucleic acid molecules to be amplified are first determined.

Although the present method is applicable to various multiplex amplification reactions, the features and advantages of the present method will be apparent in an amplification reaction for at least three target nucleic acid molecules.

The term "target nucleic acid molecule", "target molecule" or "target nucleic acid" as used herein refers to a nucleic acid molecule to be finally amplified or detected. As used herein, the term "target nucleic acid molecule" or "nucleic acid molecule" may be used interchangeably with "target nucleic acid sequence" or "nucleic acid sequence", respectively. The target nucleic acid molecule comprises a molecule in a single strand as well as in a double strand. The target nucleic acid molecule comprises a nucleic acid sequence newly produced in reactions as well as a sequence initially present in a sample.

The target nucleic acid molecule may include any DNA (gDNA and cDNA), RNA molecules and their hybrids (chimera nucleic acid). The molecule may be in either a double-stranded or single-stranded form. Where the nucleic acid as starting material is double-stranded, it is preferred to render the two strands into a single-stranded or partially single-stranded form. Methods known to separate strands includes, but not limited to, heating, alkali, formamide, urea and glycoxal treatment, enzymatic methods (e.g., helicase action), and binding proteins. For instance, strand separation can be achieved by heating at temperature ranging from 80° C. to 105° C. General methods for accomplishing this treatment are provided by Joseph Sambrook, et al., *Molecular Cloning, A Laboratory Manual*, Cold Spring Harbor Laboratory Press, Cold Spring Harbor, N.Y. (2001).

The target nucleic acid sequence includes any naturally occurring prokaryotic, eukaryotic (for example, protozoans and parasites, fungi, yeast, higher plants, lower and higher animals, including mammals and humans), viral (for example, Herpes viruses, HIV, influenza virus, Epstein-Barr virus, hepatitis virus, polio virus, etc.), or viroid nucleic acid. The nucleic acid molecule can also be any nucleic acid molecule which has been or can be recombinantly produced or chemically synthesized. Thus, the nucleic acid sequence may or may not be found in nature.

The target nucleic acid molecule should not be construed as limiting the sequence known at a given time or the sequence available as of a given time, but instead should be read to encompass the sequence that may be available or known now or at any time in the future. In other words, the target nucleic acid molecule may or may not be known at the time of practicing the present method. In case of unknown target nucleic acid, its sequence may be determined by one of conventional sequencing methods prior to performing the present method.

When the target molecule is a target nucleic acid molecule, the sample may undergo a nucleic acid extraction procedure known in the art (see Sambrook, J. et al., Molecular Cloning, A Laboratory Manual, 3rd ed. Cold Spring Harbor Press (2001)). The nucleic acid extraction process may vary depending on the type of the sample. In addition, when the extracted nucleic acid is RNA, a reverse transcription process for synthesizing cDNA can be further performed (see Sambrook, J. et al., Molecular Cloning, A Laboratory Manual, 3rd ed., Cold Spring Harbor Press (2001)).

According to an embodiment of this invention, the target nucleic acid sequence comprises a nucleotide variation.

The term "nucleotide variation" used herein refers to any single or multiple nucleotide substitutions, deletions or insertions in a DNA sequence at a particular location among contiguous DNA segments that are otherwise similar in sequence. Such contiguous DNA segments include a gene or any other portion of a chromosome. These nucleotide variations may be mutant or polymorphic allele variations. For example, the nucleotide variation detected in the present invention includes SNP (single nucleotide polymorphism), mutation, deletion, insertion, substitution and translocation. Exemplified nucleotide variation includes numerous variations in a human genome (e.g., variations in the MTHFR (methylenetetrahydrofolate reductase) gene), variations involved in drug resistance of pathogens and tumorigenesis-causing variations. The term "nucleotide variation" used herein includes any variation at a particular location in a nucleic acid sequence. In other words, the term "nucleotide variation" includes a wild type and its any mutant type at a particular location in a nucleic acid sequence.

As used herein, the expression "determining at least three target nucleic acid molecules to be amplified" refers to a procedure of determining which nucleic acid sequence to be amplified, i.e., selecting at least three target nucleic acid molecules to be amplified, among a number of nucleic acid molecules.

In one embodiment of the present invention, the target nucleic acid molecule to be amplified is at least three target nucleic acid molecules, at least four target nucleic acid molecules, at least five target nucleic acid molecules, at least six target nucleic acid molecules, at least seven target nucleic acid molecule, or at least eight target nucleic acid molecules. For example, the target nucleic acid molecule to be amplified may be 3-20, 3-18, 3-15, 3-12, 3-10, 3-8, 3-5, 4-20, 4-18, 4-15, 4-12, 4-10, 4-8, 4-5, 5-20, 5-18, 5-15, 5-12, 5-10 or 5-8 target nucleic acid molecules.

In one embodiment of the present invention, at least three primer pairs, at least four primer pairs, at least five primer pairs, at least six primer pairs, at least seven primer pairs, or at least eight primer pairs are used for amplifying at least three target nucleic acid molecules, at least four target nucleic acid molecules, at least five target nucleic acid molecules, at least six target nucleic acid molecules, at least seven target nucleic acid molecules or at least eight target nucleic acid molecules, respectively.

According to one embodiment, the number of target nucleic acid molecules to be amplified and detected by the present method is same as that of primer pairs used in the present method.

In accordance with the present invention, at least three primer pairs are prepared to amplify at least three target nucleic acid molecules, wherein each primer pair comprises a forward primer and a reverse primer. Each primer comprises a hybridizing nucleotide sequence to a corresponding target nucleic acid molecule.

According to one embodiment of the present invention, at least three primer pairs used herein is three prime pairs, four primer pairs, five primer pairs, or the like.

The term "primer" as used herein refers to an oligonucleotide, which is capable of acting as a point of initiation of synthesis when placed under conditions in which synthesis of primer extension product which is complementary to a nucleic acid strand (template) is induced, i.e., in the presence of nucleotides and an agent for polymerization, such as DNA polymerase, and at a suitable temperature and pH. Preferably, the primers are single-stranded deoxyribonucleotide molecules. The primers used in this invention may be comprised of naturally occurring dNMP (i.e., dAMP, dGM, dCMP and dTMP), modified nucleotide, or non-natural nucleotide. The primers may also include ribonucleotides.

The primer must be sufficiently long to prime the synthesis of extension products in the presence of the agent for polymerization. The exact length of the primers will depend on many factors, including temperature, application, and source of primer. The term "annealing" or "priming" as used herein refers to the apposition of an oligodeoxynucleotide or nucleic acid to a template nucleic acid, whereby the apposition enables the polymerase to polymerize nucleotides into a nucleic acid molecule which is complementary to the template nucleic acid or a portion thereof.

The term "complementary" is used herein to mean that primers or probes are sufficiently complementary to hybridize selectively to a target nucleic acid sequence under the designated annealing conditions or stringent conditions, encompassing the terms "substantially complementary" and "perfectly complementary", preferably perfectly complementary.

The term used "hybridizing" used herein refers to the formation of a double-stranded nucleic acid from complementary single stranded nucleic acids. The hybridization may occur between two nucleic acid strands perfectly matched or substantially matched with some mismatches. The complementarity for hybridization may depend on hybridization conditions, particularly temperature.

There is no intended distinction between the terms "annealing" and "hybridizing", and these terms will be used interchangeably.

The terms "a primer pair", "a pair of primers", "one primer pair", "one pair of primers" and "one type of primer pair" as used herein include a pair of forward primer and reverse primer. A primer pair can be used in an amplification reaction for one target nucleic acid molecule.

Further, a plurality of primer pairs as referred to herein, for example, (at least) two primer pairs, (at least) three primer pairs, (at least) four primer pairs, etc., means that the number of primer pairs is plural and the primer pairs are different from each other. Thus, the terms "at least three primer pairs" as used herein means that the number of primer pairs is at least three and the primer pairs are different from each other.

The expression "primer pairs are different from each other" may encompass the meaning of: (i) the primer pairs are substantially different from each other, or (ii) the primer pairs are completely different from each other.

The expression "primer pairs are substantially different from each other" means that a forward primer of one primer pair is different from a forward primer of the other primer pair, or that a reverse primer of one primer pair is different from a reverse primer of the other primer pair.

The expression "primer pairs are completely different from each other" means that a forward primer of one primer pair is different from a forward primer of the other primer pair and a reverse primer of one primer pair is different from a reverse primer of the other primer pair.

The method of the present invention generally uses at least three primer pairs which are completely different from each other, but does not preclude the use of at least three primer pairs which are substantially different from each other.

According to an embodiment, primer pairs in the present invention are completely different from each other.

Two different primer pairs may be expressed as "two primer pairs"; three different primer pairs as "three primer pairs".

Further, the expression "primers are different from each other" means that the primers are different in length, or that the primers are not represented by one sequence or one sequence containing 5 or less degenerate bases therein.

For example, when primers are designed to include degenerate bases at specific sites so as to amplify nucleic acids having some variations in a conserved region, the primers are considered to be the same primers, that is, a single primer, because they have same length of sequences and are represented by one sequence containing 5 or less degenerate bases. According to one embodiment of the present invention, the term "single or one primer" is one which has a specific length and is represented by one sequence or represented by a sequence that includes five or less, particularly four or less, more particularly three or less degenerate bases.

The IUB degenerate codes for nucleotide bases are used herein. In this code, R means either of the purine bases A or G; Y means either of the pyrimidine bases C or T; M means either of the amino bases A or C; K means either of the keto bases G or T; S means either of the stronger hydrogen binding partners C or G; W means either of the weaker hydrogen bonding partners A or T; H means either of A, T or C; B means either of G, T or C; D means either of G, A or T; V means either of G, A or C and N means either of A, C, G or T.

In the present invention, at least three primer pairs, each primer pair comprising a forward primer and a reverse primer, which are used in a multiplex amplification reaction for at least three target nucleic acid molecules, include a plurality of primers. Generally, the total number of primers is usually two times the total number of primer pairs. However, in the case that there is one or more identical primers between the primer pairs, the total number of primers may be less than two times the total number of primer pairs.

According to one embodiment of the present invention, at least three primer pairs used herein comprise 4, 5, or 6 primers.

According to one embodiment of the present invention, at least five primer pairs used herein comprise 6, 7, 8, 9, or 10 primers.

According to one embodiment of the present invention, at least seven primer pairs used herein comprise 8, 9, 10, 11, 12, 13 or 14 primers.

Conventionally, a universal base such as deoxyinosine or inosine has been widely employed as a 'degenerate base' because of its ability to pair indiscriminately with each of the four standard nucleotide bases. Particularly, primers containing inosine compensate for the high rate of degeneracy of the targeted codons and can substantially reduce overall primer degeneracy as well as false priming and nontarget gene amplification (Kilpatrick, D. R. et al., 1996. J. Clin. Microbiol. 34:2990-2996; Rossolini. G. M. et al., 1994. Mol. Cell. Probes 8:91-98). However, there has been no attempt to inhibit dimer formation in a multiplex amplification reaction by incorporating a universal base(s) such as inosine into the core region of the primer as in the present invention.

The method of the present invention utilizes a primer(s) containing universal base nucleotide(s) to reduce the formation of primer dimers, particularly both-strands extendable primer dimers and to improve target amplification efficiency. According to the present invention, placing universal base nucleotide(s) elaborately in the primer can effectively inhibit the formation of primer dimers while retaining the properties (e.g., specific binding to complementary sequence and elongation by polymerase) of a corresponding conventional primer (i.e., a primer comprising a naturally occurring nucleotide complementary to the target in place of the universal base nucleotide).

The primer prepared according to the strategy proposed by the present invention is referred to as Universal Base Primer (UBP). The term "Universal Base Primer (UBP)" as used herein refers to one in which at least one nucleotide in a primer contains a universal base instead of a naturally occurring base (A, C, G or T (U)). In the present invention, the UBP acts as an inhibitor against primer dimer formation. In particular, a primer incorporating deoxyinosine or inosine among universal bases is referred to as Inosine Primer (IPm). In contrast, the term "conventional primer" as used herein refers to a commonly used primer which consists of naturally occurring nucleotides only (A, C, G or T (U)). Primers as used herein can be synthesized in-house or by a third party for synthesizing a primer.

Incorporating a universal base(s) into a primer according to the present invention contributes to suppress primer dimer formation and increase amplification efficiency in a multiplex amplification reaction for at least three primer pairs.

For a nucleic acid amplification process, primer dimers may be formed by hybridization between some sequences of primers. Since the binding strength between a universal base and a naturally occurring base is relatively lower than that between two complementary naturally occurring bases, incorporating at least one universal base nucleotide into an appropriate position, i.e., the core region of the primer would lower the $T_m$ of the primer dimer and inhibit the formation of the primer dimer.

According to the present invention, the UBP has 1-3 universal base nucleotides. In an embodiment, the UBP has 1-2 universal base nucleotides.

The term "universal base nucleotide" refers to a nucleotide containing a universal base instead of a naturally occurring base. The term can be used interchangeable with "universal nucleotide", "universal base-containing nucleotide", "universal base-incorporating nucleotide", and the like.

Incorporation of at least four universal nucleotide nucleotides into the UBP is not desirable because it can reduce the hybridization efficiency between the target and the primer due to high abundance of universal base nucleotides. Thus, incorporation of three or less, in particular two or less universal base nucleotides is appropriate to retain a stable hybridization between the target and the primer.

According to the present invention, the UBP has 1-3 universal base nucleotides; wherein one or two of the universal base nucleotides are located in a core region ranging from $3^{rd}$ nucleotide to $6^{th}$ nucleotide at the 3'-end of the UBP.

The term "core region" as used herein refers to the optimal location range for placing one or two universal base nucleotides in the UBP to achieve inhibition of primer dimer formation, particularly both-strands extendable primer dimer formation. That is, the core region refers to a specific region within the UBP where one or two universal base nucleotides are located in order to exert maximum effect.

Both primer strands constituting the primer dimer, especially the both-strands extendable primer dimer, are consumed during the extension reaction and cannot be used to amplify the target nucleic acid molecule. The present inventors have found that placing one or more universal base nucleotides in the core region of either or both primer strands can minimize the possibility that the 3'-end portion participates in the formation of both-strands extendable primer dimers.

According to our experimental results, it was found that the amplification of the target nucleic acid molecule was largely affected by the formation of both-strands extendable primer dimers. Since the both-strands extendable primer dimers are usually produced by hybridization between the 3'-end portions of two primer strands, it was revealed that positioning one or two universal base nucleotides at the 3'-end portion is preferable to inhibit such formation of both-strands extendable primer dimers.

In the present invention, the exact position of the core region in the UBP was determined in terms of target amplification and primer dimer formation. That is, the exact position of the core region in the UBP was determined by identifying a region critical for inhibiting the formation of the primer dimer without detrimentally affecting the amplification of the target nucleic acid molecule.

According to the method of the present invention, the core region in the UBP ranges from $3^{rd}$ nucleotide to $6^{th}$ nucleotide at the 3'-end of the UBP.

In general, the first nucleotide or the second nucleotide at the 3'-end of a primer has a significant effect on the extension of the primer. For example, when the first nucleotide or the second nucleotide at the 3'-end of the primer is not complementary to the corresponding nucleotide of the target nucleic acid molecule, the first nucleotide or the second nucleotide at the 3'-end of the primer would not be hybridized to the corresponding nucleotide of the target nucleic acid molecule and the 3'-end would not be extended, which in turn may greatly reduce the target amplification efficiency. Similarly, for UBP of the present invention, positioning a universal base nucleotide at the first position or the second position at the 3'-end of the UBP reduces the binding of the first nucleotide or the second nucleotide at the 3'-end to a corresponding nucleotide of the target nucleic acid molecule, leading to the low target amplification efficiency. Therefore, according to one embodiment of the present invention, in view of target amplification efficiency, the core region where the universal nucleotide is located is from $3^{rd}$ nucleotide to a higher nucleotide (e.g., $4^{th}$, $5^{th}$, $6^{th}$, $7^{th}$ nucleotide or more) at the 3'-end of UBP.

On the other hand, the effect of both-strands extendable primer dimers on the target amplification depends on the number of complementary (overlapping) nucleotides within the primer dimer. Our experimental results reveals that the primer dimer containing four complementary nucleotides therein (the primer dimer with four overlapping nucleotides) does not significantly affect the target amplification; whereas the primer dimer-containing five complementary nucleo-tides therein-(the primer dimer with five overlapping nucleo-tides) may affect the target amplification depending on the type of target; the primer dimer containing six complementary nucleotides therein (the primer dimer with six overlapping nucleotides) has a significant effect on target amplification. Thus, in order to inhibit the formation of primer dimers having six complementary nucleotides therein, a dimer type greatly affecting the target amplification, the universal base nucleotide may be located at the $6^{th}$ nucleotide or lower.

According to the present invention, positioning the universal base nucleotide at the first nucleotide or the second nucleotide at the 3'-end of the UBP is undesirable because it decreases the target amplification efficiency. On the other hand, positioning the universal base nucleotide at the third nucleotide can inhibit the formation of primer dimers with three or more complementary nucleotides at the 3'-end of each primer strand; positioning the universal base nucleotide at the fourth nucleotide can inhibit the formation of four or more complementary nucleotides at the 3'-end of each primer strand; positioning the universal base nucleotide at the fifth nucleotide can inhibit the formation of primer dimers with five or more complementary nucleotides at the 3'-end of each primer strand; and positioning the universal base nucleotide at the sixth nucleotide can inhibit the formation of primer dimers with six or more complementary nucleotides at the 3'-end of each primer strand, thereby improving target amplification efficiency.

In accordance with an embodiment, the present method can prevent two primer strands from hybridization, and hence the formation of both-strands extendable primer dimers.

As described above, it should be noted that the formation of the primer dimers with four or less complementary nucleotides therein does not significantly affect the target amplification efficiency. For example, positioning the universal base nucleotide at the $3^{rd}$ nucleotide at the 3'-end of the UBP does not inhibit the formation of the primer dimer containing two complementary nucleotides at the 3'-end of each primer strand, but the formation of the primer dimer does not affect the target amplification efficiency. Instead, the UBP having a universal base nucleotide positioned as above can inhibit the formation of a primer dimer having three or more complementary nucleotides therein, so that it is suitable for achieving the object of the present invention.

According to one embodiment of the present invention, the core region ranges from $3^{rd}$ nucleotide to $6^{th}$ nucleotide, from $3^{rd}$ nucleotide to $5^{th}$ nucleotide, from $3^{rd}$ nucleotide to $4^{th}$ nucleotide, from $4^{th}$ nucleotide to $6^{th}$ nucleotide, from $4^{th}$ nucleotide to $5^{th}$ nucleotide, or from $5^{th}$ nucleotide to $6^{th}$ nucleotide at the 3'-end of the UBP, particularly from $3^{rd}$ nucleotide to $5^{th}$ nucleotide at the 3'-end of the UBP.

With regard to the definition of the core region and the position of the universal base nucleotide, the first nucleotide at the 3'-end of a primer refers to the nucleotide at the 3'-terminal end, i.e., the 3' ultimate nucleotide (3'-terminal nucleotide). Sequentially, the second nucleotide at the 3'-end of the UBP refers to the nucleotide at the second position from the last, i.e., the 3' penultimate nucleotide; the third nucleotide at the 3'-end of the UBP refers to the nucleotide at the third position from the last, i.e., the 3' antepenultimate nucleotide; the fourth nucleotide at the 3'-end of the UBP refers to the nucleotide at the fourth position from the last, i.e., the 3' preantepenultimate nucleotide; the fifth nucleotide at the 3'-end of the UBP refers to the nucleotide at the fifth position from the last, and the like. The description of the position applies equally to the 5'-end of the primer.

In one example, assuming a primer having the following sequence: 5'-AGNNNNNNNNNNNNNNCT-3' (A: adenine, G: guanine, N: any nucleotide, C: cytosine; T: thymine) (SEQ ID NO:61), "A" corresponds to the first nucleotide at the 5'-end of the primer, "G" to the second nucleotide at the 5'-end of the primer, "C" to the second nucleotide at the 3'-end of the primer, and "T" to the first nucleotide at the 3'-end of the primer.

In another example, assuming a primer having the following sequence: 5'-AAAAAAAAAAAAAAAAAAAAAGGGGAA-3' (SEQ ID NO:62), (A: adenine, G: guanine), the core region ranging from 3rd nucleotide to 6th nucleotide at the 3'-end is "GGGGG".

According to the present invention, the universal base nucleotides are nonconsecutive in the UBP. This means that the universal base nucleotides in the UBP are not immediately adjacent to each other.

According to the present invention, one or two universal base nucleotides can be located in the core region.

According to the present invention, the expression "the universal base nucleotides are nonconsecutive in the UBP" can be used interchangeably with the expression "the universal base nucleotides are positioned apart from each other in the UBP". The expression "the universal base nucleotides are positioned apart from each other in the UBP" as used herein means that there is(are) other nucleotide(s) between the two universal base nucleotides. For example, "the universal base nucleotides are positioned two nucleotides apart from each other" means that there are two other nucleotides between the two universal base nucleotides.

In one embodiment of the present invention, the universal base nucleotides are positioned at least 1, 2, 3, 5, 8, 10, 12, 15 and 20 nucleotides apart from each other in the UBP.

In one embodiment of the present invention, the universal base nucleotides are positioned 1-10 nucleotides apart from each other in the UBP, for example 1-8 nucleotides, 1-6 nucleotides, 1-4 nucleotides, 2-10 nucleotides, 2-8 nucleotides, 2-6 nucleotides, 2-4 nucleotides, 3-10 nucleotides, 3-8 nucleotides, 3-6 nucleotides, or 3-4 nucleotides apart from each other in the UBP.

In accordance with the present invention, other universal base nucleotide(s), except for the universal base nucleotide(s) located in the core region, if present, is located in a region ranging from $4^{th}$ nucleotide at the 5'-end of the UBP to $7^{th}$ nucleotide at the 3'-end of the UBP.

Considering that the delimitation of the core region may vary, the remainder (other universal base nucleotide(s)) can be located in a region except for the core region, three consecutive nucleotides at the 5'-end of the UBP, and two consecutive nucleotides at the 3'-end of the UBP. In other words, the remainder is located in a region ranging from $4^{th}$ nucleotide at the 5'-end of the UBP to a nucleotide immediately adjacent to (a nucleotide next to) the 5' last nucleotide of the core region.

The position of the remaining universal base nucleotide(s) which is not located in the core region is determined as follows:

(i) locating the universal base nucleotide(s) at the first nucleotide position or the second nucleotide position at the 3'-end of the UBP significantly hinders from target amplification; and (ii) locating the universal base nucleotide(s) at the first nucleotide position (5' ultimate nucleotide), the second nucleotide position (5' penultimate nucleotide) or the third nucleotide position (5' antepenultimate nucleotide) at the 5'-end of the UBP is not sufficient to improve target amplification, because the primer dimer formed by hybridization at the above position does not greatly affect the target amplification due to a short extension.

Taken together, the remainder is located in a region except for the core region, three consecutive nucleotides at the 5'-end of the UBP, and two consecutive nucleotides at the 3'-end of the UBP.

According to the present invention, when one or two of the universal base nucleotides are located in a core region ranging from $3^{rd}$ nucleotide to $6^{th}$ nucleotide at the 3'-end of the UBP, and the remainder is located in a region ranging from $4^{th}$ nucleotide at the 5'-end of the UBP to $7^{th}$ nucleotide at the 3'-end of the UBP.

According to one embodiment, when one or two of the universal base nucleotides are located in a core region ranging from $3^{rd}$ nucleotide to $5^{th}$ nucleotide at the 3'-end of the UBP, and the remainder is located in a region ranging from $4^{th}$ nucleotide at the 5'-end of the UBP to $6^{th}$ nucleotide at the 3'-end of the UBP.

Depending upon the number of universal bases in UBP, the position of one to three the universal base nucleotides in the UBP can be described as follows:

(i) Where the UBP has one universal base nucleotide:

The universal base nucleotide is located in a core region.

(ii) Where the UBP has two universal base nucleotides:

In an embodiment, two universal base nucleotides are located in a core region.

In an alternative embodiment, one universal base nucleotide is located in a core region, and the other is located in a region except for the core region, three consecutive nucleotides at the 5'-end of the UBP, and two consecutive nucleotides at the 3'-end of the UBP. In the case where the core region ranges from $3^{rd}$ nucleotide to $6^{th}$ nucleotide at the 3'-end of the UBP, the remainder is located in a region ranging from $4^{th}$ nucleotide at the 5'-end of the UBP to $7^{th}$ nucleotide at the 3'-end of the UBP. In the case where the core region ranges from $3^{rd}$ nucleotide to $5^{th}$ nucleotide at the 3'-end of the UBP, the remainder is located in a region ranging from $4^{th}$ nucleotide at the 5'-end of the UBP to $6^{th}$ nucleotide at the 3'-end of the UBP (iii) Where the UBP has three universal base nucleotides:

In an embodiment, one universal base nucleotide is located in a core region, and two universal base nucleotides are located in a region except for the core region, three consecutive nucleotides at the 5'-end of the UBP, and two consecutive nucleotides at the 3'-end of the UBP.

In an alternative embodiment, two universal base nucleotides are located in a core region, and one universal base nucleotide is located in a region except for the core region, three consecutive nucleotides at the 5'-end of the UBP, and two consecutive nucleotides at the 3'-end of the UBP.

The embodiments in which the UBP has two or three universal base nucleotides are explained in more detail, as follows:

(i) Where the UBP has two universal base nucleotides:

In an embodiment, two universal base nucleotides are located in the core region.

In another embodiment, one universal base nucleotide is located in the core region of the UBP, and the other is located within 5, 10 or more nucleotides in the 5' direction from the 5' last nucleotide of the core region of the UBP. For example, when the core region ranges from $3^{rd}$ nucleotide to $6^{th}$ nucleotide at the 3'-end of the UBP, the other is located from $11^{th}$ nucleotide to $7^{th}$ nucleotide, $12^{th}$ nucleotide to $7^{th}$ nucleotide, $13^{th}$ nucleotide to $7^{th}$ nucleotide, $14^{th}$ nucleotide to $7^{th}$ nucleotide, $15^{th}$ nucleotide to $7^{th}$ nucleotide, or $16^{th}$ nucleotide to $7^{th}$ nucleotide at the 3'-end of the UBP. In such case, the possibility that the 3' portion of the UBP hybridizes with another primer can further be reduced.

According to an alternative embodiment, one universal base nucleotide is located in the core region of the UBP, and the other is located in the 5' portion or the 3' portion of the UBP wherein the 5' portion and the 3' portion may be determined by bisection of nucleotide length of UBP. In such case, the possibility that another primer hybridize to the UBP can further be reduced.

Regarding the limitation on the location of the universal base nucleotide, one embodiment of the present invention utilizes bisecting the entire nucleotide length of the UBP. When the total length of the UBP is an even number, the UBP is evenly bisected, whereas where the total length of the UBP is an odd number, the UBP is not evenly bisected. In the case where the UBP is not evenly bisected, the addition or deletion of one nucleotide may be employed. In other words, the UBP can be bisected precisely by deleting any nucleotide at the 5'-end or by adding any imaginary nucleotide to the 5'-end. The addition or deletion of any nucleotide is intended only for exact bisection of the UBP, and thus the universal base nucleotide is not construed to be located in the added or deleted nucleotide. Alternatively, the UBP may be bisected by deleting any nucleotide at the 3'-end or by adding any imaginary nucleotide to the 3'-end.

(ii) Where the UBP has three universal base nucleotides:

According to an embodiment, one universal base nucleotide is located in the core region, and two universal nucleotides are located within 5, 10 or more nucleotides in the 5' direction from the 5' last nucleotide of the core region of the UBP. For example, when the core region ranges from $11^{th}$ nucleotide to $7^{th}$ nucleotide, $12^{th}$ nucleotide to $7^{th}$ nucleotide, $13^{th}$ nucleotide to $7^{th}$ nucleotide, $14^{th}$ nucleotide to $7^{th}$ nucleotide, $15^{th}$ nucleotide to $7^{th}$ nucleotide, or $16^{th}$ nucleotide to $7^{th}$ nucleotide at the 3'-end of the UBP at the 3'-end of the UBP.

According to an alternative embodiment, one universal base nucleotide is located in the core region of the UBP, another is located within 5, 10 or more nucleotides in the 5' direction from the 5' last nucleotide of the core region of the UBP, and the other is located in the 5' portion of the UBP wherein the 5' portion and the 3' portion may be determined by bisection of nucleotide length of UBP with or without addition or deletion of one nucleotide.

According to another embodiment, one universal base nucleotide is located in the core region of the UBP, another is located in the 5' portion, the middle portion, or the 3' portion of the UBP wherein the three portions are determined by trisection of nucleotide length of UBP with or without addition or deletion of one or two nucleotide, and the other is located in the same or different portion as the another nucleotide. For example, one universal base nucleotide is located in the core region of the UBP, another is located in the 5' portion of the UBP and the other is located in the middle portion of the UBP.

The position of the universal base as described above is intended to be illustrative, and other positions of the universal base nucleotide may be considered by one of skill in the art.

Positioning the universal base nucleotides as above enables a multiplex amplification reaction using the at least three primer pairs to generate amplification products of the target nucleic acid molecules with reduced primer dimer formation.

In particular, disposing the universal base in the 5' portion of the UBP as described above can inhibit the formation of the one-strand extendable primer dimer, and consequently prevent the consumption of components of the PCR reaction such as the polymerase and dNTPs.

According to an embodiment of the present invention, at least one of the UBPs does not comprise a degenerate base. According to another embodiment, at least 1, 2, 3, 4, 5, 6, 8, 10 or 12 of the UBPs used in the multiplex amplification reaction do not include a degenerate base. According to an embodiment of the present invention, at least 50%, 60% or 70% of the UBPs used in the multiplex amplification reaction does not comprise a degenerate base. According to an embodiment of the present invention, when the UBP has a degenerate base, the number of degenerate bases does not exceed one. According to another embodiment, all of the UBPs do not comprise a degenerate base. The incorporation of the universal base nucleotides into a primer herein can reduce the need to use degenerate bases.

According to one embodiment of the present invention, both of the forward primer and the reverse primer in the at least one primer pair, at least two primer pair, at least three primer pair, at least four primer pair or at least five primer pair among the primer pairs are UBPs.

According to one embodiment of the present invention, either or both of the forward primer and the reverse primer in each primer pair are UBPs.

According to one embodiment of the invention, at least 50%, 60%, 70%, 80% or 90% of the total number of primers used are UBPs.

According to one embodiment of the present invention, the primers are all universal base primers.

According to one embodiment of the present invention, at least three primer pairs used herein comprise at least two UBPs. Specifically, at least three primer pairs used herein comprise at least 3, at least 4, at least 5, or at least 6 UBPs.

According to one embodiment of the present invention, at least four primer pairs used herein comprise at least 3 UBPs. Specifically, at least four primer pairs used herein comprise at least 4, at least 5, at least 6, at least 7 or at least 8 UBPs.

According to one embodiment of the present invention, at least five primer pairs used herein comprise at least 3 UBPs. Specifically, at least five primer pairs used herein comprise at least 4, at least 5, at least 6, at least 7, at least 8, at least 9, or at least 10 UBPs.

According to one embodiment of the present invention, at least seven primer pairs used herein comprise at least 4 UBPs. Specifically, at least seven primer pairs used herein comprise at least 4, at least 5, at least 6, at least 7, at least 8, at least 9, at least 10, at least 11, at least 12, at least 13 or at least 14 UBPs.

The length of the primers used in the present invention may vary depending upon several factors such as convenience and cost of primer synthesis, and the accuracy and sensitivity of amplification reaction. For example, the length of the primers used in the present invention may be, without limitation, at least 12 nucleotides, at least 15 nucleotides, at least 18 nucleotides, at least 20 nucleotides, at least 22 nucleotides, at least 24 nucleotides, up to 60 nucleotides, 50 nucleotides, up to 40 nucleotides, up to 35 nucleotides, up to 30 nucleotides, or up to 25 nucleotides.

According to an embodiment of the present invention, the length of the primer is 12-60, 12-50, 12-40, 12-35, 12-30, 12-25, 15-60, 15-50, 15-40, 15-35, 15-30, 15-25, 20-60, 20-50, 20-40, 20-35, 20-30, 20-25, 22-60, 22-50, 22-40, 22-35, 22-30, 22-25, 24-60, 24-50, 24-40, 24-35, or 24-30 nucleotides, specifically 20-30 nucleotides.

According to the present invention, the universal base is selected from the group consisting of deoxyinosine, inosine, 7-deaza-2'-deoxyinosine, 2-aza-2'-deoxyinosine, 2'-OMe inosine, 2'-F inosine, deoxy 3-nitropyrrole, 3-nitropyrrole, 2'-OMe 3-nitropyrrole, 2'-F 3-nitropyrrole, 1-(2'-deoxy-beta-D-ribofuranosyl)-3-nitropyrrole, deoxy 5-nitroindole, 5-nitroindole, 2'-OMe 5-nitroindole, 2'-F 5-nitroindole, deoxy 4-nitrobenzimidazole, 4-nitrobenzimidazole, deoxy 4-aminobenzimidazole, 4-aminobenzimidazole, deoxy nebularine, 2'-F nebularine, 2'-F 4-nitrobenzimidazole, PNA-5-introindole, PNA-nebularine, PNA-inosine, PNA-4-nitrobenzimidazole, PNA-3-nitropyrrole, morpholino-5-nitroindole, morpholino-nebularine, morpholino-inosine, morpholino-4-nitrobenzimidazole, morpholino-3-nitropyrrole, phosphoramidate-5-nitroindole, phosphoramidate-nebularine, phosphoramidate-inosine, phosphoramidate-4-nitrobenzimidazole, phosphoramidate-3-nitropyrrole, 2'-O-methoxyethyl inosine, 2'-O-methoxyethyl nebularine, 2'-O-methoxyethyl 5-nitroindole, 2'-O-methoxyethyl 4-nitrobenzimidazole, 2'-O-methoxyethyl 3-nitropyrrole, and combinations thereof. More specifically, the universal base is deoxyinosine, inosine, or a combination thereof.

Step (b): Multiplex Amplification Reaction Using at Least Three Primer Pairs

A multiplex amplification reaction is then carried out by using the at least three primer pairs of step (a), the reaction comprising at least two cycles of primer annealing, primer extension and denaturation.

In step (b), the multiplex amplification reaction generates amplification products of the target nucleic acid molecules with reduced primer dimer formation.

The multiplex amplification reaction of the present invention is performed in a closed single vessel.

The multiplex amplification of target nucleic acid molecules can be performed by various primer-involved nucleic acid amplification methods known in the art, including polymerase chain reaction (PCR), ligase chain reaction (LCR) (U.S. Pat. Nos. 4,683,195 and 4,683,202; PCR Protocols: A Guide to Methods and Applications (Innis et al., eds, 1990)), strand displacement amplification (SDA) (Walker, et al. Nucleic Acids Res. 20(7):1691-6 (1992); Walker PCR Methods Appl 3(1):1-6 (1993)), transcription-mediated amplification (Phyffer, et al., J. Clin. Microbiol. 34:834-841 (1996); Vuorinen, et al., J. Clin. Microbiol. 33:1856-1859 (1995)), nucleic acid sequence-based amplification (NASBA) (Compton, Nature 350(6313):91-2 (1991)), rolling circle amplification (RCA) (Lisby, Mol. Biotechnol. 12(1):75-99 (1999); Hatch et al., Genet. Anal. 15(2):35-40 (1999)) and Q-Beta Replicase (Lizardi et al., BiolTechnology 6:1197 (1988)).

The multiplex amplification reaction of the present invention can be performed according to a real-time PCR method (see U.S. Pat. Nos. 5,210,015, 5,538,848 and 6,326,145). The term "multiplex amplification" means simultaneously amplifying multiplex DNA targets in a single polymerase reaction mixture.

The target nucleic acid molecules for multiplex amplification may include any DNA (gDNA and cDNA), RNA molecules and their hybrids (chimera nucleic acid). The sequence may be in either a double-stranded or single-stranded form. Where the nucleic acid as starting material is double-stranded, it is preferred to render the two strands into a single-stranded or partially single-stranded form. Methods known to separate strands includes, but not limited to, heating, alkali, formamide, urea and glycoxal treatment, enzymatic methods (e.g., helicase action), and binding proteins. For instance, strand separation can be achieved by heating at temperature ranging from 80° C. to 105° C. General methods for accomplishing this treatment are provided by Joseph Sambrook, et al., *Molecular Cloning, A Laboratory Manual*, Cold Spring Harbor Laboratory Press, Cold Spring Harbor, N.Y. (2001).

Where a mRNA is employed as starting material, a reverse transcription step is necessary prior to performing annealing step, details of which are found in Joseph Sambrook, et al., Molecular Cloning, A Laboratory Manual, Cold Spring Harbor Laboratory Press, Cold Spring Harbor, N.Y. (2001); and Noonan, K. F. et al., Nucleic Acids Res. 16:10366 (1988)). For reverse transcription, an oligonucleotide dT primer hybridizable to mRNA, a random hexamer, or an oligonucleotide complementary to target nucleic acid molecule can be used.

The oligonucleotide dT primer is comprised of dTMPs, one or more of which may be replaced with other dNMPs so long as the dT primer can serve as primer. Reverse transcription can be done with reverse transcriptase that has RNase H activity. If one uses an enzyme having RNase H activity, it may be possible to omit a separate RNase H digestion step by carefully choosing the reaction conditions.

The primer used in the present invention is hybridized or annealed at one site of the template to form a double-stranded structure. Suitable conditions for nucleic acid hybridization to form such a double-stranded structure are described in Joseph Sambrook, et al., Molecular Cloning, A Laboratory Manual, Cold Spring Harbor Laboratory Press, Cold Spring Harbor, N.Y. (2001) and Haymes, B. D., et al., Nucleic Acid Hybridization, A Practical Approach, IRL Press, Washington, D.C. (1985).

A variety of DNA polymerases can be used in the amplification step of the present invention, including, for example, Klenow fragment of *E. coli* DNA polymerase I, a thermostable DNA polymerase and bacteriophage 17 DNA polymerase. Particularly, the polymerase is a thermostable DNA polymerase which may be obtained from a variety of bacterial species, including *Thermus aquaticus* (Taq), *Thermus thermophilus* (Tth), *Thermus filiformis, Thermis flavus, Thermococcus literalis, Thermus antranikianii, Thermus caldophilus, Thermus chliarophilus, Thermus flavus, Thermus igniterrae, Thermus lacteus, Thermus oshimai, Thermus ruber; Thermus rubens, Thermus scotoductus, Thermus silvanus, Thermus* species Z05, *Thermus* species sps 17, *Thermus thermophilus, Thermotoga maritima, Thermotoga neapolitana, Thermosipho africanus, Thermococcus litoralis, Thermococcus barossi, Thermococcus gorgonarius, Thermotoga maritima, Thermotoga neapolitana, Thermo siphoafricanus, Pyrococcus furiosus*(Pfu), *Pyrococcus woesei, Pyrococcus horikoshii, Pyrococcus abyssi, Pyrodictium occultum, Aquifex pyrophilus* and *Aquifex aeolieus.* Most of these enzymes can be isolated from the bacteria itself or commercially available. In addition, the polymerase used in the present invention can be obtained from cells expressing high levels of the cloning gene encoding the polymerase.

When the polymerization reaction is carried out, components necessary for the reaction may be provided in excess in the reaction vessel. The excess of the components required for the amplification reaction means an amount such that the amplification reaction is not substantially restricted to the concentration of the component. Cofactors such as $Mg^{2+}$, and dNTPs such as dATP, dCTP, dGTP and dTTP, are required to be provided to a reaction mixture in an amount to achieve the desired degree of amplification.

All enzymes used in the amplification reaction may be active under the same reaction conditions. In fact, buffers ensure that all enzymes are close to optimal reaction conditions. Therefore, the multiplex amplification process of the present invention can be carried out in a single reaction without changing the conditions such as the addition of reactants.

In the present invention, annealing or hybridization is carried out under stringent conditions that allow specific binding between the target nucleic acid sequence and the primer. The stringent conditions for annealing are sequence-dependent and vary with environmental variables.

According to one embodiment of the present invention, the primer annealing in the multiplex amplification reaction in step (b) is carried out at 50° C. or higher.

The amplification reaction in the method of the present invention can be carried out at a relatively high annealing temperature in order to prevent primer dimer formation, even though a UBP contains a universal base. In the multiplex amplification reaction of step (b), the primer annealing is carried out at a temperature of 50° C. or higher, 52° C. or higher, 55° C. or higher, or 57° C. or higher. Specifically, in the multiplex amplification reaction of step (b), the primer annealing is performed at 85° C. or lower, at 80° C. or lower, 75° C. or lower, 70° C. or lower, 65° C. or lower and 60° C. or lower, for example, 50-85° C., 50-80° C., 50-75° C., 52-75° C., 55-75° C., 50-70° C., 52-70° C., 55-70° C., 50-60° C., 52-60° C., 55-60° C. or 57-60° C.

A multiplex amplification reaction for at least three target nucleic acid molecules using a universal base primer(s) is carried out in the presence of at least three additional probes for detecting the presence of each target nucleic acid molecule. Each of the at least three additional probes has a hybridizing sequence to corresponding target nucleic acid molecule and is located between a forward primer and a reverse primer for amplifying the target nucleic acid molecule. The use of the probes in the multiplex amplification reaction using the UBP(s) of the present invention can further increase the detection specificity of the target nucleic acid molecule. The use of probes can be carried out according to various methods known in the art. Examples of such methods include the TaqMan™ probe method (U.S. Pat. No. 5,210,015), molecular beacon method (Tyagi et al., Nature Biotechnology v. 14 Mar. 1996), CPT (Duck P, et al. Biotechniques, 9: 142-148(1990)), LNA method (U.S. Pat. No. 6,977,295), Plexor method (Sherrill C B et al., Journal of the American Chemical Society, 126: 4550-4556 (2004)), Hybeacons™ (D. J. French, et al., Molecular and Cellular Probes (2001) 13, 363-374 and U.S. Pat. No. 7,348,141), dual-labeled self-quenched probes (U.S. Pat. No. 5,876, 930), hybridization probes (Bernard P S, et al., Clin Chem 2000, 46, 147-148), PTOCE (WO cleavage and extension; WO 2012/096523), PCE-SH (PTO Cleavage and Extension-Dependent Signaling Oligonucleotide Hybridization; WO 2013/115442), PCE-NH (PTO Cleavage and Extension-Dependent Non-Hybridization; WO 2014/104818) and CER method (WO 2011/037306).

According to one embodiment of the present invention, the at least three probes do not have a universal base nucleotide.

According to one embodiment of the present invention, probes may or may not contain a label. According to one embodiment of the present invention, depending on the presence of target nucleic acid molecules, probes may mediate a downstream reaction (e.g. PTOCE method).

The method of the present invention exhibits reduced primer dimer formation compared to the amplification reaction using conventional primers.

Specifically, the reduced formation of the primer dimers can be assessed by measuring the change in signals accompanied by formation of the primer dimer. Alternatively, a change in Ct values, a change in maximum RFUs, or a change ratio of signals may be used for assessing the reduced formation of the primer dimers.

In one embodiment, the reduced formation of the primer dimers can be assessed by comparing the Ct values between a reaction using the UBP of the present invention in the absence of target nucleic acid molecule and a reaction using conventional primers consisting of naturally occurring nucleotides in the absence of target nucleic acid molecule. For such comparison, a conventional primer can be used which contains naturally occurring nucleotides which are complementary to nucleotides in a target nucleic acid molecule, instead of the universal base nucleotides.

According to an embodiment of the present invention, the Ct value obtained from a reaction using a primer pair containing the UBP in the absence of a target nucleic acid molecule (i.e., Ct value of primer dimer) is increased by 1 or more, as compared with that using a primer pair consisting of conventional primers in the absence of a target nucleic acid molecule. The Ct value obtained from a reaction using a primer pair containing the UBP in the absence of a target nucleic acid molecule is increased by 2 or more, 3 or more, 4 or more, 5 or more, 6 or more, e.g., 3 to 20, 5 to 15, or 8 to 12, as compared with that using a primer pair consisting of conventional primers in the absence of a target nucleic acid molecule.

The term "Ct value of primer dimer" means the Ct value calculated from the amplification curve of primer dimers, which is obtained by an amplification reaction using a PCR reaction mixture in the absence of any template. Thus, the increase in the Ct value of the primer dimer indicates that the formation of the primer dimer is inhibited or reduced.

Methods for obtaining Ct values are known in the art (see Joseph Sambrook, et al., Molecular Cloning, A Laboratory Manual, Cold Spring Harbor Laboratory Press, Cold Spring Harbor, NY (2001)).

When the inhibition or reduction of primer dimer formation is highly effective, the Ct value in the amplification curve of the primer dimer may not be obtained due to low amplification of the primer dimer. In this case, the Ct value of primer dimer is considered to be increased by 1 or more.

The method of the present invention exhibits increased target amplification efficiency as compared to a target amplification reaction using a conventional primer instead of the UBP. The increased target amplification efficiency may be assessed by comparing the differences between signals obtained by amplifying a target nucleic acid molecule using a primer containing naturally occurring nucleotides and signals obtained by amplifying a target nucleic acid molecule using a universal base primer (For example, a change in Ct values, a change in maximum RFUs, a change ratio of signals, etc.).

As used herein, the term "amplification efficiency" includes any value as long as it can indicate the efficiency of an amplification reaction.

Amplification efficiency can be calculated by any of a variety of methods known in the art.

In an embodiment, the amplification efficiency can be estimated by calculating the amplification rate on the basis of a linear regression slope of a dilution row and calculating the amplification efficiency based on the following equation (Higuchi et al., 1993; Rasmussen, 2001):

$$E = 10^{-1/slope} \qquad \text{Equation 1}$$

wherein E represents the amplification efficiency; slope represents the slope of the standard curve in which Ct values are plotted against initial copy numbers of the target.

In another embodiment, amplification efficiency can be estimated by any of the programs known in the art. For example, amplification efficiency can be calculated by LinRegPCR for the analysis of quantitative RT-PCR (qPCR) data (version 2017.1).

When LinRegPCR is employed to obtain amplification efficiency, the raw (i.e., not baseline-corrected) PCR data are used in the analysis. Baseline correction is carried out with a baseline trend based on a selection of early cycles. The PCR efficiency for each individual sample is derived from the slope of the regression line fitted to a subset of base-corrected data points in the log-linear phase using LinRegPCR. The program uses typically an individual window-of-linearity, but, in the case of some samples, the upper and lower limit of the individual window-of-linearity may be set.

The efficiency for the reaction using UBP obtained by one of the above methods can be compared to the efficiency for the reaction using conventional primers. The efficiency of the reaction using UBPs can be expressed as an increase rate relative to the reaction using conventional primers. The increase rate can be calculated by the following equation:

$$\text{Increase rate of efficiency (\%)} = \qquad \text{Equation 2}$$
$$[(\text{efficiency for an reaction using UBP/efficiency}$$
$$\text{for a reaction using conventional primers}) - 1] * 100$$

According to one embodiment of the present invention, amplification of a target nucleic acid molecule by using the UBP in a multiplex amplification reaction exhibits an increase rate of efficiency of 3%, 5%, 10%, 20%, 30%, 40%, 50%, 60%, 70%, 80%, 90%, 100%, 200%, 300% or more, as compared to those using primers consisting of naturally occurring nucleotides.

According to one embodiment of the present invention, the amplification efficiency of each reaction is calculated by LinRegPCR, and the increase rate of efficiency for the reaction using UBP is calculated in comparison with the reaction using the conventional primers.

In a second aspect of the present invention, there is provided method for reducing primer dimer formation in a multiplex amplification reaction for at least three target nucleic acid molecules, comprising the steps of:

(a) determining at least three target nucleic acid molecules to be amplified;

(b) determining nucleotide sequences of at least three primer pairs, each primer pair comprising a forward primer and a reverse primer; wherein each primer comprises a hybridizing nucleotide sequence to a corresponding target nucleic acid molecule;

(c) replacing 1-3 nucleotides in either or both of primers in at least one primer pair among the at least three primer pairs with universal base nucleotides to prepare universal base primers (UBPs); wherein the replacement with the universal base nucleotides allows the inhibition of primer dimer formation; wherein the UBP has 1-3 universal base nucleotides; wherein one or two of the universal base nucleotides are located in a core region ranging from $3^{rd}$ nucleotide to $6^{th}$ nucleotide at the 3'-end of the UBP, and the remainder is located in a region ranging from $4^{th}$ nucleotide at the 5'-end of the UBP to $7^{th}$ nucleotide at the 3'-end of the UBP; wherein the universal base nucleotides are nonconsecutive in the UBP; and (d) performing a multiplex amplification reaction comprising at least two cycles of primer annealing, primer extension and denaturation by using the at least three primer pairs; wherein the multiplex amplification reaction generates amplification products of the target nucleic acid molecules with reduced primer dimer formation.

In an embodiment of the present invention, the core region ranges from $3^{rd}$ nucleotide to $5^{th}$ nucleotide at the 3'-end of the UBP.

In an embodiment of the present invention, both of primers in the at least one primer pair are UBPs.

In an embodiment of the present invention, either or both of primers in each primer pair are UBPs.

In an embodiment of the present invention, at least 50% of the total number of primers used are UBPs.

In an embodiment of the present invention, at least one of the UBPs does not comprise a degenerate base.

In an embodiment of the present invention, at least five primer pairs are used for amplifying at least five target nucleic acid molecules.

In an embodiment of the present invention, the primer annealing in the multiplex amplification reaction is performed at 50° C. or higher.

In an embodiment of the present invention, the method exhibits a target amplification efficiency of at least 3% higher than that of using primer(s) containing naturally occurring nucleotides (A, C, G or T (U)) complementary to the target nucleic acid sequence instead of the at least one UBPs.

In an embodiment of the present invention, the Ct value obtained from a reaction using a primer pair containing the UBP in the absence of a target nucleic acid molecule is increased by 1 or more, as compared with that using a primer pair consisting of conventional primers in the absence of a target nucleic acid molecule.

In an embodiment of the present invention, the multiplex amplification reaction is performed in the presence of at least three additional probes for detecting the presence of the target nucleic acid molecules; wherein each of the at least three probes comprises a hybridizing nucleotide sequence to the target nucleic acid molecule to be amplified and is located between the forward primer and the reverse primer.

In an embodiment of the present invention, the at least three probes do not have a universal base nucleotide.

In an embodiment of the present invention, the universal base nucleotide is selected from the group consisting of deoxyinosine, inosine, 7-deaza-2'-deoxyinosine, 2-aza-2'-deoxyinosine, 2'-OMe inosine, 2'-F inosine, deoxy 3-nitropyrrole, 3-nitropyrrole, 2'-OMe 3-nitropyrrole, 2'-F 3-nitropyrrole, 1-(2'-deoxy-beta-D-ribofuranosyl)-3-nitropyrrole, deoxy 5-nitroindole, 5-nitroindole, 2'-OMe 5-nitroindole, 2'-F 5-nitroindole, deoxy 4-nitrobenzimidazole, 4-nitrobenzimidazole, deoxy 4-aminobenzimidazole, 4-aminobenzimidazole, deoxy nebularine, 2'-F nebularine, 2'-F 4-nitrobenzimidazole, PNA-5-introindole, PNA-nebularine, PNA-inosine, PNA-4-nitrobenzimidazole, PNA-3-nitropyrrole, morpholino-5-nitroindole, morpholino-nebularine, morpholino-inosine, morpholino-4-nitrobenzimidazole, morpholino-3-nitropyrrole, phosphoramidate-5-nitroindole, phosphoramidate-nebularine, phosphoramidate-inosine, phosphoramidate-4-nitrobenzimidazole, phosphoramidate-3-nitropyrrole, 2'-O-methoxyethyl inosine, 2'-O-methoxyethyl nebularine, 2'-O-methoxyethyl 5-nitroindole, 2'-O-methoxyethyl 4-nitrobenzimidazole, 2'-O-methoxyethyl 3-nitropyrrole, and combinations thereof.

In an embodiment of the present invention, the universal base nucleotide comprises deoxyinosine, inosine, or a combination thereof.

The second aspect of the present invention, "a method for reducing primer dimer formation in a multiplex amplification reaction" is an application of the first aspect as mentioned above. Thus, the common descriptions between them are omitted in order to avoid undue redundancy leading to the complexity of this specification.

In a third aspect of the present invention, there is provided a kit for amplifying at least three target nucleic acid molecules with reduced primer dimer formation in a multiplex amplification reaction, comprising:

(a) at least three primer pairs, each primer pair comprising a forward primer and a reverse primer; wherein each primer comprises a hybridizing nucleotide sequence to a corresponding target nucleic acid molecule; wherein either or both of primers in at least one primer pair are universal base primers (UBPs); wherein the UBP has 1-3 universal base nucleotides; wherein one or two of the universal base nucleotides are located in a core region ranging from $3^{rd}$ nucleotide to $6^{th}$ nucleotide at the 3'-end of the UBP, and the remainder is located in a region ranging from 4th nucleotide at the 5'-end of the UBP to $7^{th}$ nucleotide at the 3'-end of the UBP; wherein the universal base nucleotides are nonconsecutive in the UBP; and (b) a nucleic acid polymerase.

In a fourth aspect of the present invention, there is provided use of a kit for amplifying at least three target nucleic acid molecules with reduced primer dimer formation in a multiplex amplification reaction in the performance of the method of claim 1, wherein the kit comprises:

(a) at least three primer pairs, each primer pair comprising a forward primer and a reverse primer; wherein each primer comprises a hybridizing nucleotide sequence to a corresponding target nucleic acid molecule; wherein either or both of primers in at least one primer pair are universal base primers (UBPs); wherein the UBP has 1-3 universal base nucleotides; wherein one or two of the universal base nucleotides are located in a core region ranging from $3^{rd}$ nucleotide to $6^{th}$ nucleotide at the 3'-end of the UBP, and the remainder is located in a region ranging from $4^{th}$ nucleotide at the 5'-end of the UBP to $3^{rd}$ nucleotide at the 3'-end of the UBP; wherein the universal base nucleotides are nonconsecutive in the UBP; and (b) a nucleic acid polymerase.

The kit or use of the kit for amplifying at least three target nucleic acid molecules of the present invention is for carrying out the method of the present invention described above, and the common descriptions between them are omitted in order to avoid undue redundancy leading to the complexity of this specification.

Optionally, the kit of the present invention may comprise reagents necessary for PCR reactions, such as buffers, DNA polymerase, DNA polymerase cofactors and deoxyribonucleotide-5'-triphosphate. Optionally, the kit of the present invention may further comprise various polynucleotide molecules, reverse transcriptase, various buffers and reagents, and an antibody that inhibits the activity of DNA polymerase. In addition, the kit of the present invention may further comprise reagents necessary for positive and negative control reactions. The optimal amount of reagents used in a particular reaction may be readily determined by one of ordinary skill in the art. Typically, the kit of the present invention comprises the components described above in a separate package or compartment.

In a fifth aspect of the present invention, there is provided a computer readable storage medium containing instructions to configure a processor to: design at least three primer pairs, each primer pair comprising a forward primer and a reverse primer; wherein each primer comprises a hybridizing nucleotide sequence to a corresponding target nucleic acid molecule; wherein either or both of primers in at least one primer pair are universal base primers (UBPs); wherein the UBP has 1-3 universal base nucleotides; wherein one or two of the universal base nucleotides are located in a core region ranging from $3^{rd}$ nucleotide to $6^{th}$ nucleotide at the 3'-end of the UBP, and the remainder is located in a region ranging from 4th nucleotide at the 5'-end of the UBP to $7^{th}$ nucleotide at the 3'-end of the UBP; wherein the universal base nucleotides are nonconsecutive in the UBP.

Since the storage medium is intended to perform the present methods in a computer, the common descriptions between them are omitted in order to avoid undue redundancy leading to the complexity of this specification.

The present method described above is implemented in a processor, such as a processor in a stand-alone computer, a network attached computer or a data acquisition device such as a real-time PCR machine.

The types of the computer readable storage medium include various storage medium such as CD-R, CD-ROM, DVD, flash memory, floppy disk, hard drive, portable HDD, USB, magnetic tape, MINIDISC, nonvolatile memory card, EEPROM, optical disk, optical storage medium, RAM, ROM, system memory and web server.

The instructions to configure the processor to perform the present invention may be included in a logic system. The instructions may be downloaded and stored in a memory module (e.g., hard drive or other memory such as a local or attached RAM or ROM), although the instructions can be provided on any software storage medium such as a portable HDD, USB, floppy disk, CD and DVD. A computer code for implementing the present invention may be implemented in a variety of coding languages such as C, C++, Java, Visual Basic, VBScript, JavaScript, Perl and XML. In addition, a variety of languages and protocols may be used in external and internal storage and transmission of data and commands according to the present invention.

The features and advantages of the present invention are summarized as follows:
    (a) Inhibition of dimer formation in a multiplex nucleic acid amplification reaction The method of the present invention inhibits the formation of nonspecific amplification products, particularly primer dimers in an effective manner in a multiplex amplification reaction for at least three target nucleic acid molecules.
    (b) Enhancement of nucleic acid amplification efficiency
    Formation of the primer dimers, particularly completely extended primer dimers, prevents the primers from participating in the amplification of the target. Also, as the amplification progresses, the non-target amplification products produced by the primer dimer competitively bind to a target nucleic acid molecule and consumes the amplification components comprising primers, thereby reducing the amplification efficiency for the target. The method of the present invention inhibits such dimer formation at the initial cycle, which in turn enhances nucleic acid amplification efficiency.
    (c) Increased sensitivity to a low concentration of target
    If target nucleic acid molecules are initially present in small amounts in the sample, the target nucleic acid molecule may not be detected due to a lower amplification amount than primer pairs. However, when the dimer formation is reduced by the method of the present invention, target nucleic acid molecules can be detected, even if they are present in small amounts, thereby improving the sensitivity.
    (d) Easy construction of a primer set for multiplex nucleic acid amplification with improved amplification efficiency
    It is considerably time-consuming and inefficient to repeatedly adjust the hybridization site of the primer and the sequence and length of the primer in order to inhibit the dimer formation between the primers and to improve the amplification efficiency. In particular, for a multiplex amplification using a plurality of primers, the change of the sequence or length of one primer should be performed in consideration of the possibility of dimer formation with other primers. For this reason, it is difficult to adjust the entire primers toward reduced dimer formation and increased amplification efficiency in a multiplex amplification reaction.

In contrast, the method of the present invention is capable of inhibiting dimer formation without changing the hybridization site of the primer or changing the sequence or length of the primer, which is useful in constructing a primer set with inhibited dimer formation for multiplex amplification reaction.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1: Identification of the Type of Primer Dimer Affecting Dimer Amplification and Target Amplification We have examined the effect of the type of primer dimer and the length of complementary nucleotides in the primer dimer on dimer amplification and target amplification.
<1-1> Primer Dimer Type for Promoting Dimer Amplification Primer dimers that can be inadvertently generated in a multiplex amplification reaction are classified into three types, depending on whether each primer strand is extended or not: (i) non-extendable primer dimer; (ii) one-strand extendable primer dimer; and (iii) both-strands extendable primer dimer (see FIG. 2).

First, non-extendable primer dimer includes those in which both primer strands following hybridization are not extended by a nucleic acid polymerase. Such type may be formed by hybridization between 5' portions of the two primers (see the top row of FIG. 2). Second, one-strand extendable primer dimer includes those in which one of two primer strands following hybridization is extended by a nucleic acid polymerase. Such type may be formed by hybridization between the 3' portion of one primer and the middle portion of another primer (see the middle row of FIG. 2). Third, both-strands extendable primer dimer includes those in which both primer strands following hybridization are extended by a nucleic acid polymerase. Such type may be formed by hybridization between the 3' portions of two primers (see the bottom row of FIG. 2).

To simulate the formation of the three types of primer dimers, conventional primers (UP-R1, SEQ ID NO: 1; NG-F4, SEQ ID NO: 12) were first prepared for hybridizing target nucleic acid sequences, genomic DNAs of *Ureaplasma parvum* (UP) and *Neisseria gonorrhoeae* (NG). Then, additional primers capable of forming one of non-extendable primer dimer, one-strand extendable primer dimer and both-strands extendable primer dimer with the conventional primers were prepared. The primers for dimer formation were designed to have various lengths of complementary nucleotides to UP-R1 (SEQ ID NO: 1) and NG-F4 (SEQ ID NO: 12).

Specifically, three primers (referred to as UP-N-1, UP-N-2 and UP-N-3 for UP, respectively; NG-N-1, NG-N-2 and NG-N-3 for NG, respectively) for forming non-extendable primer dimers with UP-R1 or NG-F4 were prepared in such a manner that they have no protruding nucleotides workable as a template for a conventional primer and their 3'-ends were blocked for preventing their extension. They were prepared to have 11, 13, or 15 complementary nucleotides to a conventional primer.

Also, three primers (referred to as UP-P-1, UP-P-2 and UP-P-3 for UP, respectively; NG-P-1, NG-P-2 and NG-P-3 for NG, respectively) for forming one-strand extendable primer dimers with UP-R1 or NG-F4 were prepared in such a manner that they provide nucleotides working as a template for a conventional primer but their 3'-ends were blocked for preventing their extension. Particularly, they were prepared to have a 3' portion of 5, 7, or 9 nucleotides complementary to a 3' portion of a conventional primer.

Further, four primers (referred to as UP-C-1, UP-C-2, UP-C-3 and UP-C-4 for UP, respectively; NG-C-1, NG-C-2, UP-C-3 and UP-C-4 for NG, respectively) for forming both-strands extendable primer dimers with UP-R1 or NG-F4 were prepared in such a manner that they have, at their 3' portion, 4, 5, 6 or 7 nucleotides complementary to a 3' portion of a conventional primer and their 3'-ends were not blocked for their extension.

Consequently, primer sets #1 to #20, each comprising one of UP-R1 and NG-F4 and one of the primers for dimer formation described above were prepared for forming the three types of primer dimers.

The sequences of primers used in this Example are provided in Tables 1 and 2, respectively.

TABLE 1

| Primer dimer type | Set Name (overlap) | Primer name | Sequence | SEQ ID NO |
|---|---|---|---|---|
| Non-extendable primer dimer | Primer set #1 (11 mer) | UP-R1 | 5'-GGTTCTCAAGCAACAATATCAGCT-3' | 1 |
| | | UP-N-1 | 5'-<u>AGCTGATATTG</u>[C3 spacer]-3' | 2 |
| | Primer set #2 (13 mer) | UP-R1 | 5'-GGTTCTCAAGCAACAATATCAGCT-3' | 1 |
| | | UP-N-2 | 5'-<u>AGCTGATATTGTT</u>[C3 spacer]-3' | 3 |
| | Primer set #3 (15 mer) | UP-R1 | 5'-GGTTCTCAAGCAACAATATCAGCT-3' | 1 |
| | | UP-N-3 | 5'-<u>AGCTGATATTGTTGC</u>[C3 spacer]-3' | 4 |
| One-strand extendable primer dimer | Primer set #4 (5 mer) | UP-R1 | 5'-GGTTCTCAAGCAACAATATCAGCT-3' | 1 |
| | | UP-P-1 | 5'-TTGGCTTGGCTTGGCTT<u>AGCTG</u> [C3 spacer]-3' | 5 |
| | Primer set #5 (7 mer) | UP-R1 | 5'-GGTTCTCAAGCAACAATATCAGCT-3' | 1 |
| | | UP-P-2 | 5'-TTGGCTTGGCTTGGCTT<u>AGCTGAT</u> [C3 spacer]-3' | 6 |
| | Primer set #6 (9 mer) | UP-R1 | 5'-GGTTCTCAAGCAACAATATCAGCT-3' | 1 |
| | | UP-P-3 | 5'-TTGGCTTGGCTTGGCTT<u>AGCTATAT</u> [C3 spacer]-3' | 7 |
| Both-strands extendable primer dimer | Primer set #7 (4 mer) | UP-R1 | 5'-GGTTCTCAAGCAACAATATCAGCT-3' | 1 |
| | | UP-C-1 | 5'-TTGGCTTGGCTTGGCTT<u>AGCT</u>-3' | 8 |
| | Primer set #8 (5 mer) | UP-R1 | 5'-GGTTCTCAAGCAACAATATCAGCT-3' | 1 |
| | | UP-C-2 | 5'-TTGGCTTGGCTTGGCTT<u>AGCTG</u>-3' | 9 |
| | Primer set #9 (6 mer) | UP-R1 | 5'-GGTTCTCAAGCAACAATATCAGCT-3' | 1 |
| | | UP-C-3 | 5'-TTGGCTTGGCTTGGCTT<u>AGCTGA</u>-3' | 10 |
| | Primer set #10 (7 mer) | UP-R1 | 5'-GGTTCTCAAGCAACAATATCAGCT-3' | 1 |
| | | UP-C-4 | 5'-TTGGCTTGGCTTGGCTT<u>AGCTGAT</u>-3' | 11 |

(Underlined letters indicate the complementary sequences to UP-R1)

TABLE 2

| Primer dimer type | Set (overlap) | Primer name | Sequence | SEQ ID NO |
|---|---|---|---|---|
| Non-extendable primer dimer | Primer set #11 (11 mer) | NG-F4 NG-N-1 | 5'-GCGGACAGTTGTTTTTCGACT-3' 5'-AGTCGAAAAAC[C3 spacer]-3' | 12 13 |
| | Primer set #12 (13 mer) | NG-F4 NG-N-2 | 5'-GCGGACAGTTGTTTTTCGACT-3' 5'-AGTCGAAAAACAA[C3 spacer]-3' | 12 14 |
| | Primer set #13 (15 mer) | NG-F4 NG-N-3 | 5'-GCGGACAGTTGTTTTTCGACT-3' 5'-AGTCGAAAAACAACT[C3 spacer]-3' | 12 15 |
| One-strand extendable primer dimer | Primer set #14 (5 mer) | NG-F4 NG-P-1 | 5'-GCGGACAGTTGTTTTTCGACT-3' 5'-TTGGCTTGGCTTGGCTTAGTCG [C3 spacer]-3' | 12 16 |
| | Primer set #15 (7 mer) | NG-F4 NG-P-2 | 5'-GCGGACAGTTGTTTTTCGACT-3' 5'-TTGGCTTGGCTTGGCTTAGTCGAA [C3 spacer]-3' | 12 17 |
| | Primer set #16 (9 mer) | NG-F4 NG-P-3 | 5'-GCGGACAGTTGTTTTTCGACT-3' 5'-TTGGCTTGGCTTGGCTTAGTCGAAAA [C3 spacer]-3' | 12 18 |
| Both-strands extendable primer dimer | Primer set #17 (4 mer) | NG-F4 NG-C-1 | 5'-GCGGACAGTTGTTTTTCGACT-3' 5'-TTGGCTTGGCTTGGCTTAGTC-3' | 12 19 |
| | Primer set #18 (5 mer) | NG-F4 NG-C-2 | 5'-GCGGACAGTTGTTTTTCGACT-3' 5'-TTGGCTTGGCTTGGCTTAGTCG-3' | 12 20 |
| | Primer set #19 (6 mer) | NG-F4 NG-C-3 | 5'-GCGGACAGTTGTTTTTCGACT-3' 5'-TTGGCTTGGCTTGGCTTAGTCGA-3' | 12 21 |
| | Primer set #20 (7 mer) | NG-F4 NG-C-4 | 5'-GCGGACAGTTGTTTTTCGACT-3' 5'-TTGGCTTGGCTTGGCTTAGTCGAA-3' | 12 22 |

(Underlined letters indicate the complementary sequences to NG-F4)

In this Example, real-time PCR using SYBR® Green I (Invitrogen, USA), intercalating dye, was employed to detect primer dimer formation in the absence of any target nucleic acid sequence. When primer dimer is formed and amplified, inactivated SYBR® Green I is incorporated into primer dimers and then becomes activated to fluoresce. An amplification curve can be obtained by measuring signals from the activated dyes in primer dimers. Taq DNA polymerase having a 5' nuclease activity was used for primer dimer amplification.

The real-time PCR was conducted in the final volume of 20 μl containing each primer set (3 pmole of one of primers (SEQ ID NOs: 1 and 12) and 10 pmole of one of primers (SEQ ID Nos: 2-11 and 13-22)), 2 μl of 10×SYBR® Green I, and 5 μl of 4× Master Mix [final, 200 μM dNTPs, 2 mM MgCl₂, 2 U of Taq DNA polymerase]. The tubes containing the reaction mixture were placed in the real-time thermocycler (CFX96, Bio-Rad) for 5 min at 50° C., denatured for 15 min at 95° C. and subjected to 50 cycles of 10 sec at 95° C., 60 sec at 57° C., 10 sec at 72° C. The detection of signals was performed at 57° C. at each cycle.

Figure 3:
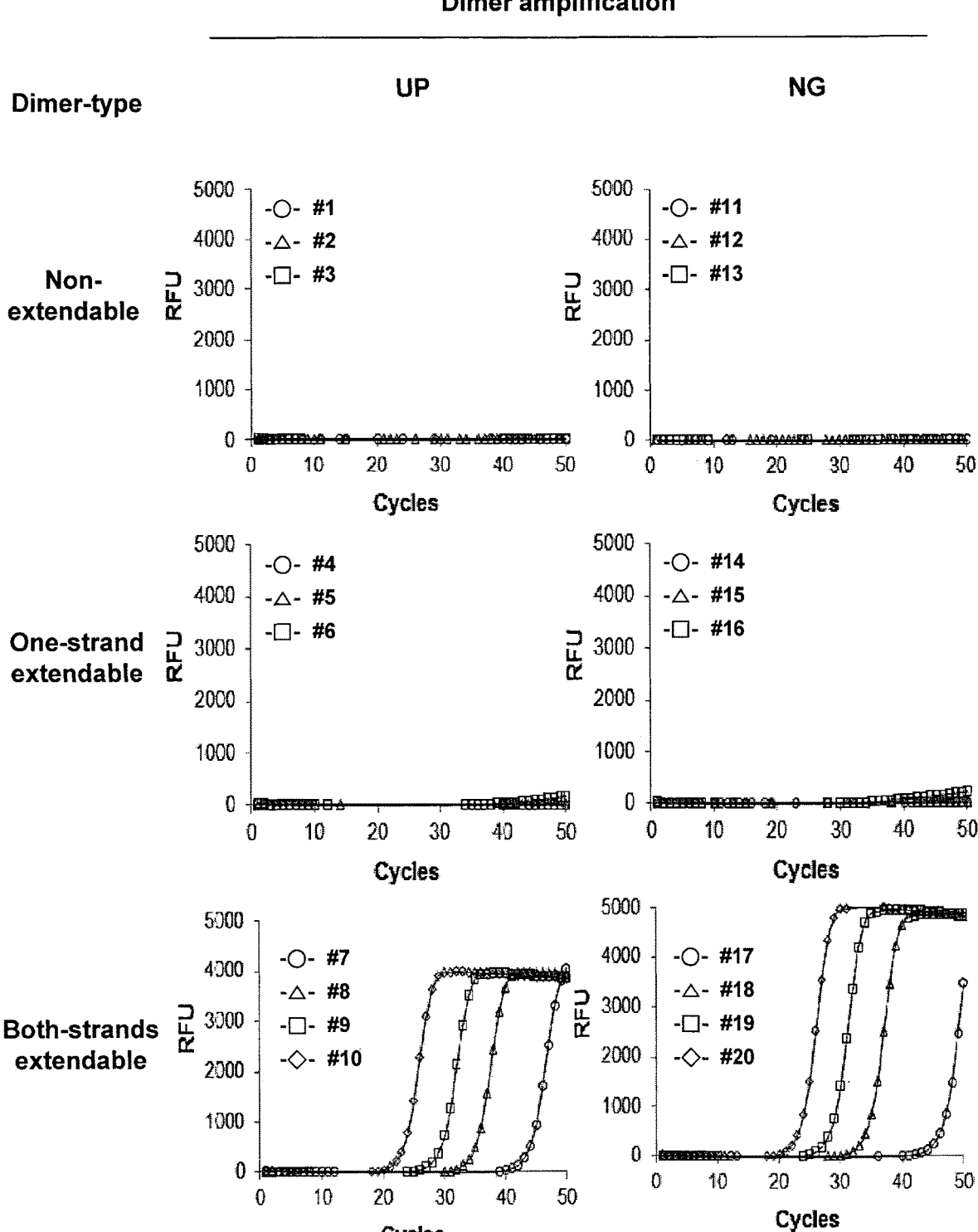
FIG. 3 shows amplification curves for primer dimers, obtained by using primer sets #1-3 (top left) and #11-13 (top right) for forming non-extendable primer dimers, primer sets #4-6 (middle left) and #14-16 (middle right) for forming one-strand extendable primer dimers, and primer sets #7-10 (bottom left) and #17-20 (bottom right) for forming both-strands extendable primer dimers, respectively.

The amplification curves obtained from the experiment above are shown in FIG. 3.

As seen in FIG. 3, amplification curves for primer dimers were not observed with primer sets #1-3 and #11-13 for forming non-extendable primer dimers (see top row of FIG. 3) and primer sets #4-6 and #14-16 for forming one-strand extendable primer dimers (see middle row of FIG. 3).

In contrast, amplification curves for primer dimers were observed with primer sets #7-10 and #17-20 for forming both-strands extendable primer dimers (see bottom row of FIG. 3). In particular, the longer length of complementary sequences within primer dimers led to earlier dimer amplification.

These results indicate that among the three types of primer dimers, both-strands extendable primer dimers promote dimer amplification, and that the length of 4-7 complementary nucleotides in the primer dimer accounts for dimer amplification.

<1-2> Primer Dimer Type for Affecting Target Amplification

The type of primer dimers affecting target amplification, i.e., inhibiting target amplification, was investigated.

A forward primer and a reverse primer (SEQ ID NOs: 23 and 1 for UP; SEQ ID Nos: 12 and 24 for NG) for amplifying a target nucleic acid sequence were first prepared. Then, additional primers (SEQ ID NOs: 2-11) capable of forming each type of primer dimers with one of the forward and reverse primers were prepared. Subsequently, the forward primer and the reverse primer were combined with one of the additional primers to obtain various primer sets #21-40. A primer set without additional primers capable of forming each type of primer dimer was used as a control.

The primer sets used in this Example are provided in Tables 3 and 4.

TABLE 3

| Primer dimer type | Set Name (overlap) | Primer name | Sequence | SEQ ID NO |
|---|---|---|---|---|
| No primer dimer | UP control primer set | UP-F1 | 5'-GCACAATTTGGATCATTAAAAGGT-3' | 23 |
| | | UP-R1 | 5'-GGTTCTCAAGCAACAATATCAGCT-3' | 1 |
| Non-extendable primer dimer | Primer set #21 (11 mer) | UP-F1 | 5'-GCACAATTTGGATCATTAAAAGGT-3' | 23 |
| | | UP-R1 | 5'-GGTTCTCAAGCAACAATATCAGCT-3' | 1 |
| | | UP-N-1 | 5'-AGCTGATATTG[C3 spacer]-3' | 2 |
| | Primer set #22 (13 mer) | UP-F1 | 5'-GCACAATTTGGATCATTAAAAGGT-3' | 23 |
| | | UP-R1 | 5'-GGTTCTCAAGCAACAATATCAGCT-3' | 1 |
| | | UP-N-2 | 5'-AGCTGATATTGTT[C3 spacer]-3' | 3 |
| | Primer set #23 (15 mer) | UP-F1 | 5'-GCACAATTTGGATCATTAAAAGGT-3' | 23 |
| | | UP-R1 | 5'-GGTTCTCAAGCAACAATATCAGCT-3' | 1 |
| | | UP-N-3 | 5'-AGCTGATATTGTTGC[C3 spacer]-3' | 4 |
| One-strand extendable primer dimer | Primer set #24 (5 mer) | UP-F1 | 5'-GCACAATTTGGATCATTAAAAGGT-3' | 23 |
| | | UP-R1 | 5'-GGTTCTCAAGCAACAATATCAGCT-3' | 1 |
| | | UP-P-1 | 5'-TTGGCTTGGCTTGGCTTAGCTG [C3 spacer]-3' | 5 |
| | Primer set #25 (7 mer) | UP-F1 | 5'-GCACAATTTGGATCATTAAAAGGT-3' | 23 |
| | | UP-R1 | 5'-GGTTCTCAAGCAACAATATCAGCT-3' | 1 |
| | | UP-P-2 | 5'-TTGGCTTGGCTTGGCTTAGCTGAT [C3 spacer]-3' | 6 |
| | Primer set #26 (9 mer) | UP-F1 | 5'-GCACAATTTGGATCATTAAAAGGT-3' | 23 |
| | | UP-R1 | 5'-GGTTCTCAAGCAACAATATCAGCT-3' | 1 |
| | | UP-P-3 | 5'-TTGGCTTGGCTTGGCTTAGCTGATAT [C3 spacer]-3' | 7 |
| Both-strands extendable primer dimer | Primer set #27 (4 mer) | UP-F1 | 5'-GCACAATTTGGATCATTAAAAGGT-3' | 23 |
| | | UP-R1 | 5'-GGTTCTCAAGCAACAATATCAGCT-3' | 1 |
| | | UP-C-1 | 5'-TTGGCTTGGCTTGGCTTAGCT-3' | 8 |
| | Primer set #28 (5 mer) | UP-F1 | 5'-GCACAATTTGGATCATTAAAAGGT-3' | 23 |
| | | UP-R1 | 5'-GGTTCTCAAGCAACAATATCAGCT-3' | 1 |
| | | UP-C-2 | 5'-TTGGCTTGGCTTGGCTTAGCTG-3' | 9 |
| | Primer set #29 (6 mer) | UP-F1 | 5'-GCACAATTTGGATCATTAAAAGGT-3' | 23 |
| | | UP-R1 | 5'-GGTTCTCAAGCAACAATATCAGCT-3' | 1 |
| | | UP-C-3 | 5'-TTGGCTTGGCTTGGCTTAGCTGA-3' | 10 |
| | Primer set #30 (7 mer) | UP-F1 | 5'-GCACAATTTGATCATTAAAAGGT-3' | 23 |
| | | UP-R1 | 5'-GGTTCTCAAGCAACAATATCAGCT-3' | 1 |
| | | UP-C-4 | 5'-TTGGCTTGGCTTGGCTTAGCTGAT-3' | 11 |

(Underlined letters indicate the complementary sequences to UP-R1)

TABLE 4

| Primer dimer type | Set Name (overlap) | Primer name | Sequence | SEQ ID NO |
|---|---|---|---|---|
| No primer dimer | NG control Primer set | NG-F4 | 5'-GCGGACAGTTGTTTTTCGACT-3' | 12 |
| | | NG-R2 | 5'-GTCGTATCCGCATCCGTCAA-3' | 24 |
| Non-extendable primer dimer | Primer set #31 (11 mer) | NG-F4 | 5'-GCGGACAGTTGTTTTTCGACT-3' | 12 |
| | | NG-R2 | 5'-GTCGTATCCGCATCCGTCAA-3' | 24 |
| | | NG-N-1 | 5'-AGTCGAAAAAC[C3 spacer]-3' | 13 |
| | Primer set #32 (13 mer) | NG-F4 | 5'-GCGGACAGTTGTTTTTCGACT-3' | 12 |
| | | NG-R2 | 5'-GTCGTATCCGCATCCGTCAA-3' | 24 |
| | | NG-N-2 | 5'-AGTCGAAAAACAA[C3 spacer]-3' | 14 |
| | Primer set #33 (15 mer) | NG-F4 | 5'-GCGGACAGTTGTTTTTCGACT-3' | 12 |
| | | NG-R2 | 5'-GTCGTATCCGCATCCGTCAA-3' | 24 |
| | | NG-N-3 | 5'-AGTCGAAAAACAACT[C3 spacer]-3' | 15 |
| One-strand extendable primer dimer | Primer set #34 (5 mer) | NG-F4 | 5'-GCGGACAGTTGTTTTTCGACT-3' | 12 |
| | | NG-R2 | 5'-GTCGTATCCGCATCCGTCAA-3' | 24 |
| | | NG-P-1 | 5'-TTGGCTTGGCTTGGCTTAGTCG [C3 spacer]-3' | 16 |
| | Primer set #35 (7 mer) | NG-F4 | 5'-GCGGACAGTTGTTTTTCGACT-3' | 12 |
| | | NG-R2 | 5'-GTCGTATCCGCATCCGTCAA-3' | 24 |
| | | NG-P-2 | 5'-TTGGCTTGGCTTGGCTTAGTCGAA [C3 spacer]-3' | 17 |
| | Primer set #36 (9 mer) | NG-F4 | 5'-GCGGACAGTTGTTTTTCGACT-3' | 12 |
| | | NG-R2 | 5'-GTCGTATCCGCATCCGTCAA-3' | 24 |
| | | NG-P-3 | 5'-TTGGCTTGGCTTGGCTTAGTCGAAAA [C3 spacer]-3' | 18 |

TABLE 4 -continued

| Primer dimer type | Set Name (overlap) | Primer name | Sequence | SEQ ID NO |
|---|---|---|---|---|
| Both- | Primer set | NG-F4 | 5'-GCGGACAGTTGTTTTTCGACT-3' | 12 |
| strands | #37 | NG-R2 | 5'-GTCGTATCCGCATCCGTCAA-3' | 24 |
| extendable | (4 mer) | NG-C-1 | 5'-TTGGCTTGGCTTGGCTTAGTC-3' | 19 |
| primer | Primer set | NG-F4 | 5'-GCGGACAGTTGTTTTTCGACT-3' | 12 |
| dimer | #38 | NG-R2 | 5'-GTCGTATCCGCATCCGTCAA-3' | 24 |
| | (5 mer) | NG-C-2 | 5'-TTGGCTTGGCTTGGCTTAGTCG-3' | 20 |
| | Primer set | NG-F4 | 5'-GCGGACAGTTGTTTTTCGACT-3' | 12 |
| | #39 | NG-R2 | 5'-GTCGTATCCGCATCCGTCAA-3' | 24 |
| | (6 mer) | NG-C-3 | 5'-TTGGCTTGGCTTGGCTTAGTCGA-3' | 21 |
| | Primer set | NG-F4 | 5'-GCGGACAGTTGTTTTTCGACT-3' | 12 |
| | #40 | NG-R2 | 5'-GTCGTATCCGCATCCGTCAA-3' | 24 |
| | (7 mer) | NG-C-4 | 5'-TTGGCTTGGCTTGGCTTAGTCGAA-3' | 22 |

(Underlined letters indicate the complementary sequences to NG-F4)

In this Example, a TaqMan probe was used to detect target amplification as a signal generating means. Where a target nucleic acid is present, a TaqMan probe is cleaved and a labeled fragment is released. A TaqMan probe for each target nucleic acid sequence was labeled with a fluorescent reporter molecule at its 5'-end and a quencher molecule at its 3'-end (SEQ ID NOs: 25 and 26). An amplification curve can be obtained by measuring signals from the labeled fragment.

The sequences of probes additionally used in this Example are provided in Table 5 below.

TABLE 5

| Name | Sequence | SEQ ID NO |
|---|---|---|
| UP-P1 | 5'-[FAM]CCCAGCTATTGCACATGGTGTTGAT[BHQ-1]-3' | 25 |
| NG-P2 | 5'-[CAL Fluor Red 610]TGTACGGCTCCGTTGTGGCGGT[BHQ-2]-3' | 26 |

(BHQ: Black Hole Quencher)
(FAM and CAL Fluor Red 610: fluorescent reporter molecules)

The real-time PCR was conducted in the final volume of 20 μl containing each primer set (3 pmole of forward primer, 3 pmole of reverse primer and 10 pmole of primer for forming primer dimer), 3 pmole of a TaqMan probe, a target nucleic acid sequence (0.1 pg of UP or 0.1 pg of NG), and 5 μl of 4× Master Mix [final, 200 μM dNTPs, 2 mM MgCl$_2$, 2 U of Taq DNA polymerase]. The tubes containing the reaction mixture were placed in the real-time thermocycler (CFX96, Bio-Rad) for 5 min at 50° C., denatured for 15 min at 95° C. and subjected to 50 cycles of 10 sec at 95° C., 60 sec at 57° C., 10 sec at 72° C. The detection of signals was performed at 95° C. at each cycle.

Figure 4:
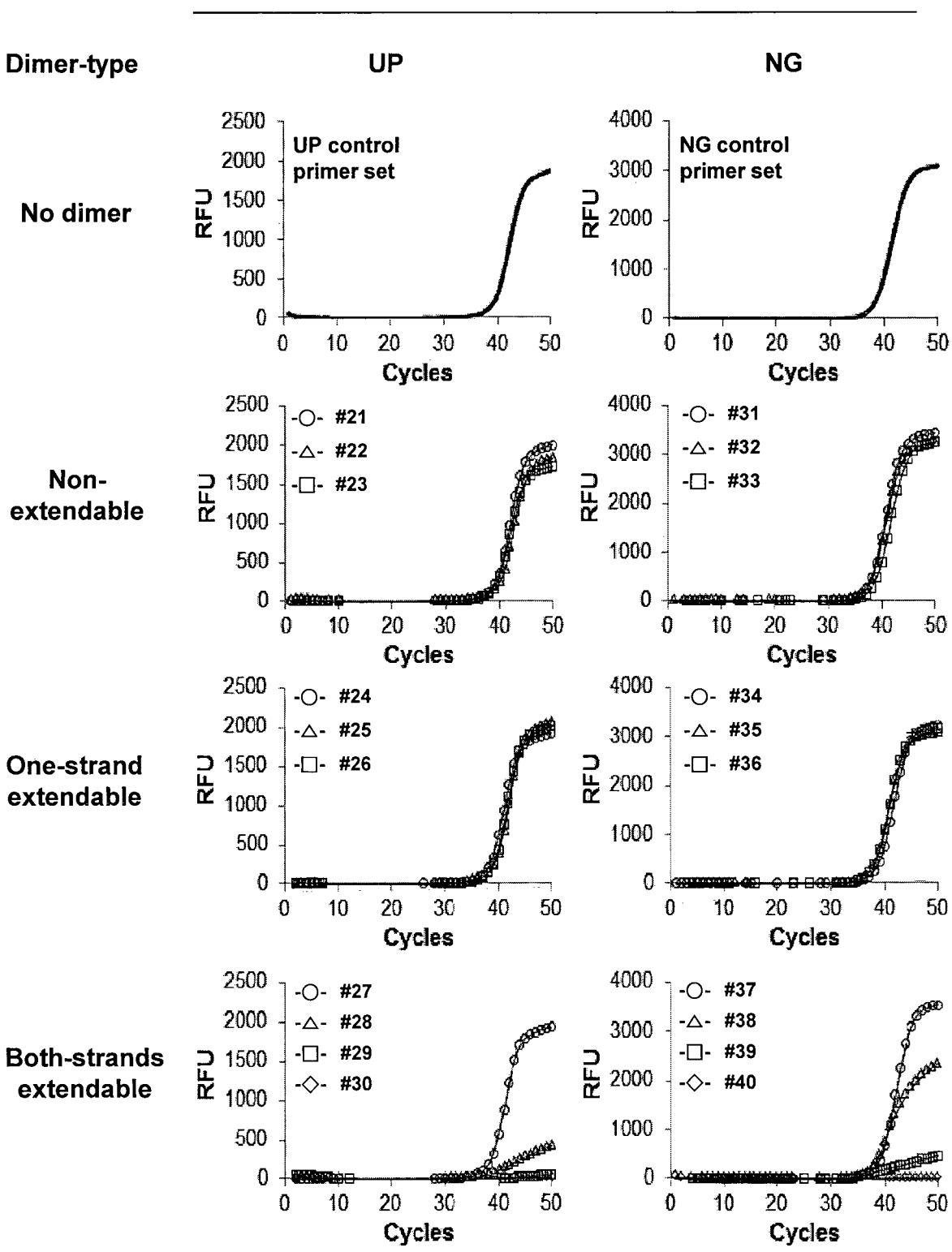
FIG. 4 shows amplification curves for target nucleic acid molecules (UP and NG), obtained by using UP control primer set and NG control primer set ($1^{st}$ row); primer sets #21-23 and #31-33 for forming non-extendable primer dimers ($2^{nd}$ row), primer sets #24-26 and #34-36 for forming one-strand extendable primer dimers ($3^{rd}$ row), and primer sets #27-30 and #37-40 for forming both-strands extendable primer dimers ($4^{th}$ row), respectively.

The amplification curves obtained from the experiments above are shown in FIG. 4.

As shown in FIG. 4, the formation of non-extendable primer dimers (primer sets #21-23 and #31-33; 2nd row) and one-strand extendable primer dimers (primer sets #23-26 and #34-36; 3rd row) did not significantly affect the amplification of the target nucleic acid molecules, whereas the formation of both-strands extendable primer dimer (primer sets #27-30 and #37-40; 4th row) significantly affect the amplification of the target nucleic acid molecules, as compared with those using control primer sets.

To better understand the effect of primer dimer on target amplification, $\Delta C_T$ values were calculated as below:

$\Delta C_T = [C_T$ in a reaction with primers for forming primer dimer] $-$ $[C_T$ in a reaction without primers for forming primer dimer]

The CT value was obtained by applying a threshold 500; $\Delta C_T$ value more than 1.0 was considered to indicate that amplification of a target nucleic acid molecule is inhibited by a primer dimer.

The $\Delta C_T$ values calculated are provided in Table 6 below.

TABLE 6

| | Length of Complementary sequence (mer) | UP | | NG | |
|---|---|---|---|---|---|
| Dimer-type | in primer dimers | $C_T$ | $\Delta C_T$ | $C_T$ | $\Delta C_T$ |
| No primer dimer | — | 38.69 | — | 38.56 | — |
| Non-extendable | 11 | 38.25 | −0.44 | 37.67 | −0.89 |
| primer dimers | 13 | 39.02 | 0.33 | 37.84 | −0.72 |
| | 15 | 38.48 | −0.21 | 38.67 | 0.11 |
| One-strand extendable | 5 | 37.46 | −1.23 | 38.78 | 0.22 |
| primer dimers | 7 | 38.18 | −0.51 | 38.02 | −0.54 |
| | 9 | 38.1 | −0.59 | 38.01 | −0.55 |
| Both-strands extendable | 4 | 37.63 | −1.06 | 39.04 | 0.48 |
| primer dimers | 5 | 41.14 | 2.45 | 38.64 | 0.08 |
| | 6 | N/A | N/A | 46.97 | 8.41 |
| | 7 | N/A | N/A | N/A | N/A |

As shown in Table 6, non-extendable primer dimers and one-strand extendable primer dimers led to $\Delta C_T$ values not more than 1.0, indicating the formation of non-extendable primer dimers and one-strand extendable primer dimers does not significantly affect target amplification.

In contrast, both-strands extendable primer dimers having complementary sequences of at least 6-mer (for both UP and NG) led to $\Delta C_T$ values more than 1.0, indicating the formation of both-strands extendable primer dimers, in particular having at least 6 complementary nucleotides in a dimer, hinders target amplification.

From the results of Examples <1-1> and <1-2>, it would be concluded that the formation of the both-strands extendable primer dimers having 5 or less complementary nucleotides therein promotes dimer amplification but does not significantly inhibit target amplification; the formation of the both-strands extendable primer dimers having 6 or more complementary nucleotides therein promotes dimer ampli-fication as well as inhibits target amplification.

Accordingly, in order to prevent inhibition of target amplification due to extendable primer dimers having 6 or more complementary nucleotides in their 3'-end portions, it was expected that it would be effective to position a universal base (e.g., deoxyinosine) to $6^{th}$ nucleotide or lower nucleotide ($5^{th}$, $4^{th}$ $3^{rd}$, etc.) at the 3'-end of a primer.

Example 2: Evaluation of the Effects of UBPs with Universal Base Nucleotides at Various Positions on Dimer Amplification and Target Amplification <2-1> Effects of UBPs with Deoxyinosines at Various Positions on Dimer Formation In this Example, the effects of UBPs with universal bases at various positions on the amplification of both-strands extendable primer dimers were compared with that of conventional primers.

For this experiment, one of two conventional primer pairs identified to form both-strands extendable primer dimers ((i) UP-R1 (SEQ ID NO: 1) in primer set #9; (ii) NG-F4 (SEQ ID NO: 12) in primer set #19) were modified to prepare various UBPs. Specifically, UBPs were prepared to contain one deoxyinosine at $2^{nd}$, $3^{rd}$, $4^{th}$, $5^{th}$, $6^{th}$, $7^{th}$, and $8^{th}$ position at its 3'-end by replacing a naturally occurring nucleotide at $2^{nd}$, $3^{rd}$, $4^{th}$, $5^{th}$, $6^{th}$, $7^{th}$, and $8^{th}$ position at its 3'-end with deoxyinosine.

One of the two conventional primer pairs (UP-C-3 (SEQ ID NO: 10) or NG-C-3 (SEQ ID NO: 23)) was combined with one of the UBPs to obtain various primer sets (referred to as primer sets #9A-9G and #19A-19G).

The primer sets used herein are provided in Table 7 below.

TABLE 7

| Primer set | Primer name | Sequence | SEQ ID NO |
|---|---|---|---|
| Primer set #9 (Conventional) | UP-R1 | 5'-GGTTCTCAAGCAACAATATCAGCT-3' | 1 |
| | UP-C-3 | 5'-TTGGCTTGGCTTGGCTT<u>AGCTGA</u>-3' | 10 |
| Primer set #9A (UBP) | UP-IR-2 | 5'-GGTTCTCAAGCAACAATATCAGIT-3' | 27 |
| | UP-C-3 | 5'-TTGGCTTGGCTTGGCTT<u>AGCTGA</u>-3' | 10 |
| Primer set #9B (UBP) | UP-IR-3 | 5'-GGTTCTCAAGCAACAATATCAICT-3' | 28 |
| | UP-C-3 | 5'-TTGGCTTGGCTTGGCTT<u>AGCTGA</u>-3' | 10 |
| Primer set #9C (UBP) | UP-IR-4 | 5'-GGTTCTCAAGCAACAATATCIGCT-3' | 29 |
| | UP-C-3 | 5'-TTGGCTTGGCTTGGCTT<u>AGCTGA</u>-3' | 10 |
| Primer set #9D (UBP) | UP-IR-5 | 5'-GGTTCTCAAGCAACAATATIAGCT-3' | 30 |
| | UP-C-3 | 5'-TTGGCTTGGCTTGGCTT<u>AGCTGA</u>-3' | 10 |
| Primer set #9E (UBP) | UP-IR-6 | 5'-GGTTCTCAAGCAACAATAICAGCT-3' | 31 |
| | UP-C-3 | 5'-TTGGCTTGGCTTGGCTT<u>AGCTGA</u>-3' | 10 |
| Primer set #9F (UBP) | UP-IR-7 | 5'-GGTTCTCAAGCAACAATITCAGCT-3' | 32 |
| | UP-C-3 | 5'-TTGGCTTGGCTTGGCTT<u>AGCTGA</u>-3' | 10 |
| Primer set #9G (UBP) | UP-IR-8 | 5'-GGTTCTCAAGCAACAAIATCAGCT-3' | 33 |
| | UP-C-3 | 5'-TTGGCTTGGCTTGGCTT<u>AGCTGA</u>-3' | 10 |
| Primer set #19 (Conventional) | NG-F4 | 5'-GCGGACAGTTGTTTTCGACT-3' | 12 |
| | NG-C-3 | 5'-TTGGCTTGGCTTGGCTT<u>AGTCGA</u>-3' | 21 |
| Primer set #19A (UBP) | NG-IF-2 | 5'-GCGGACAGTTGTTTTCGAIT-3' | 34 |
| | NG-C-3 | 5'-TTGGCTTGGCTTGGCTT<u>AGTCGA</u>-3' | 21 |
| Primer set #19B (UBP) | NG-IF-3 | 5'-GCGGACAGTTGTTTTCGICT-3' | 35 |
| | NG-C-3 | 5'-TTGGCTTGGCTTGGCTT<u>AGTCGA</u>-3' | 21 |
| Primer set #19C (UBP) | NG-IF-4 | 5'-GCGGACAGTTGTTTTCIACT-3' | 36 |
| | NG-C-3 | 5'-TTGGCTTGGCTTGGCTT<u>AGTCGA</u>-3' | 21 |
| Primer set #19D (UBP) | NG-IF-5 | 5'-GCGGACAGTTGTTTTIGACT-3' | 37 |
| | NG-C-3 | 5'-TTGGCTTGGCTTGGCTT<u>AGTCGA</u>-3' | 21 |
| Primer set #19E (UBP) | NG-IF-6 | 5'-GCGGACAGTTGTTTICGACT-3' | 38 |
| | NG-C-3 | 5'-TTGGCTTGGCTTGGCTT<u>AGTCGA</u>-3' | 21 |
| Primer set #19F (UBP) | NG-IF-7 | 5'-GCGGACAGTTGTTTITCGACT-3' | 39 |
| | NG-C-3 | 5'-TTGGCTTGGCTTGGCTT<u>AGTCGA</u>-3' | 21 |
| Primer set #19G (UBP) | NG-IF-8 | 5'-GCGGACAGTTGTTITTCGACT-3' | 40 |
| | NG-C-3 | 5'-TTGGCTTGGCTTGGCTT<u>AGTCGA</u>-3' | 21 |

(Underlined letters in UP-C-3 indicate the complementary sequences to UP-R1; and Underlined letters in NG-C-3 indicate the complementary sequences to NG-F4)

The real-time PCR was conducted in the final volume of 20 µl containing each primer set (3 pmole of one of a conventional primer UP-R1 (SEQ ID NO: 2) and UBPs (SEQ ID NOs: 27-33) and 10 pmole of UP-C-3 (SEQ ID NO: 10), or 3 pmole of one of a conventional primer NG-F4 (SEQ ID NO: 13) or UBPs (SEQ ID NOs: 34-40) and 10 pmole of NG-C-3 (SEQ ID NO: 21)), 2 µl of 10×SYBR® Green I, and 5 µl of 4× Master Mix [final, 200 µM dNTPs, 2 mM MgCl₂, 2 U of Taq DNA polymerase]. The tubes containing the reaction mixture were placed in the real-time thermocycler (CFX96, Bio-Rad) for 5 min at 50° C., denatured for 15 min at 95° C. and subjected to 50 cycles of 10 sec at 95° C., 60 sec at 57° C., 10 sec at 72° C. The detection of signals was performed at 57° C. at each cycle.

Figure 5A:
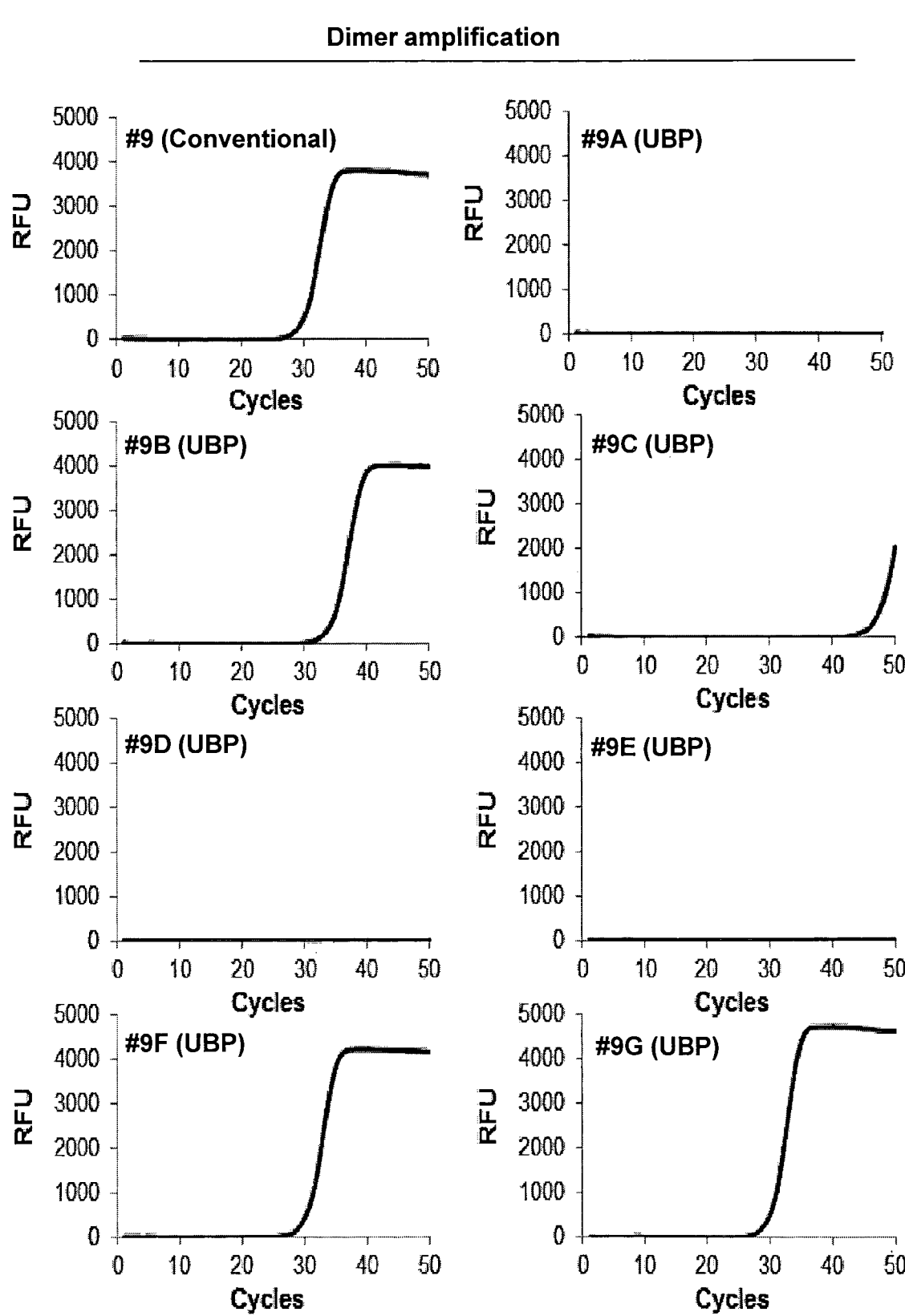
FIG. 5A shows amplification curves for primer dimers, obtained by using a primer set #9 ($1^{st}$ row, left), a primer set #9A ($1^{st}$ row, right), a primer set #9B ($2^{nd}$ row, left), a primer set #9C ($2^{nd}$ row, right), a primer set #9D ($3^{rd}$ row, left), a primer set #9E ($3^{rd}$ row, right), a primer set #9F ($4^{th}$ row, left), and a primer set #9G ($4^{th}$ row, right), respectively.
Figure 5B:
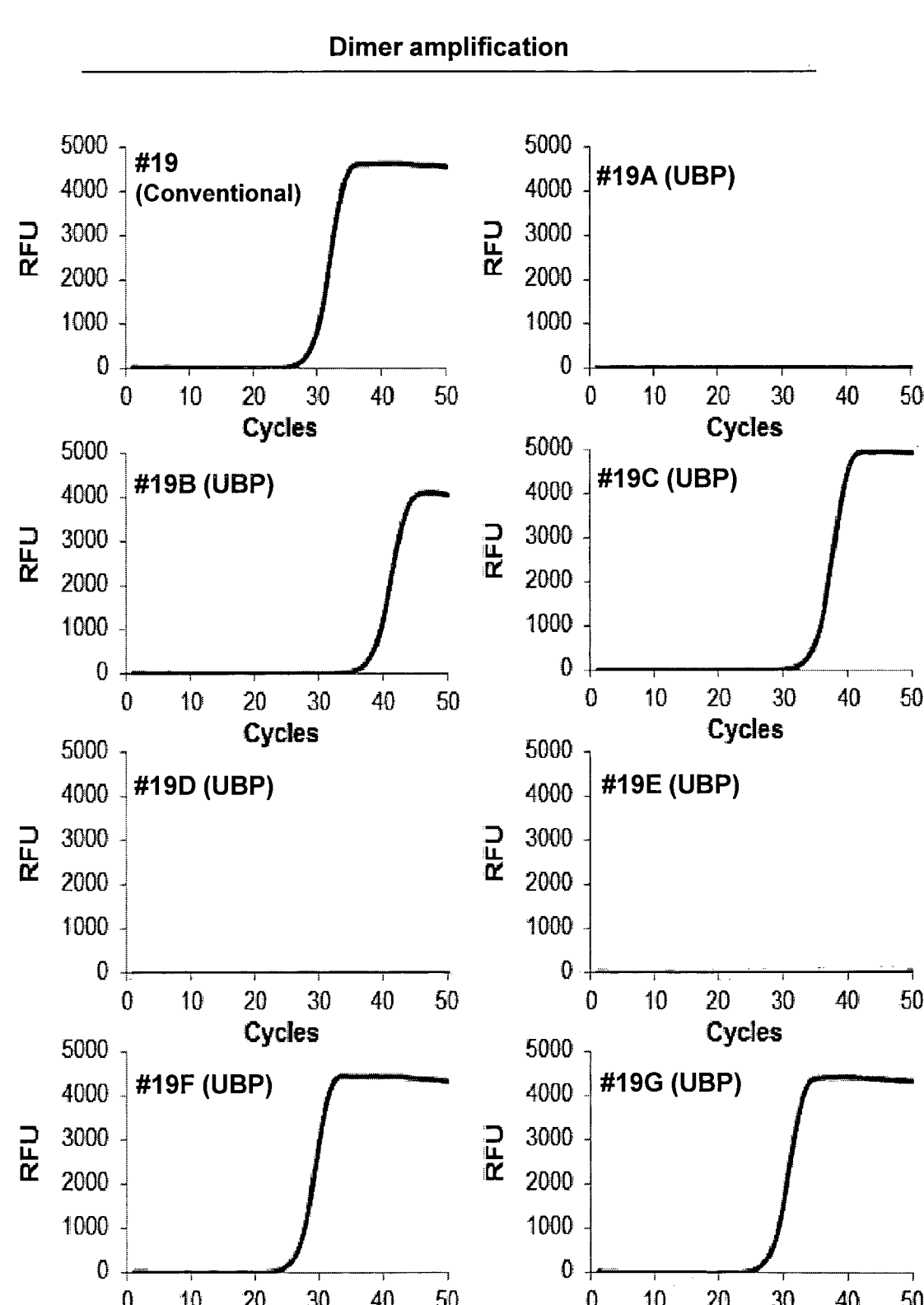
FIG. 5B shows amplification curves for primer dimers, obtained by using a primer set #19 ($1^{st}$ row, left), a primer set #19A ($1^{st}$ row, right), a primer set #19B ($2^{nd}$ row, left), a primer set #19C ($2^{nd}$ row, right), a primer set #19D ($3^{rd}$ row, left), a primer set #19E ($3^{rd}$ row, right), a primer set #19F ($4^{th}$ row, left), and a primer set #19G ($4^{th}$ row, right), respectively.

The amplification curves for primer dimer obtained above are shown in FIGS. 5A and 5B.

As shown in FIGS. 5A and 5B, amplification curves for primer dimers were not observed or were generated later with the primer sets #9A-9E and #19A-19E (comprising UBPs with deoxyinosines at $2^{nd}$, $3^{rd}$, $4^{th}$, $5^{th}$ and $6^{th}$ positions), whereas amplification curves for primer dimer were observed with the primer sets #9F, #9G, #19F and #19G (comprising UBPs with deoxyinosines at $7^{th}$ and $8^{th}$ positions).

To better understand the effect of UBP on inhibition of primer dimer formation, $\Delta C_T$ values were calculated as below:

$$\Delta C_T = [C_T \text{ for } UBP\text{-containing primer set}] - [C_T \text{ for convention primer set}]$$

The CT value was obtained by applying a threshold 500; $\Delta C_T$ value more than 1.0 was considered to indicate that dimer amplification is inhibited by UBP.

The $\Delta C_T$ values calculated are provided in Table 8 below.

TABLE 8

| Primer set | UP | | Primer set | NG | |
| | $C_T$ | $\Delta C_T$ | | $C_T$ | $\Delta C_T$ |
|---|---|---|---|---|---|
| Primer set #9 (Conventional) | 29.98 | — | Primer set #19 (Conventional) | 29.09 | — |
| Primer set #9A (UBP; $2^{nd}$) | N/A | N/A | Primer set #19A (UBP; $2^{nd}$) | N/A | N/A |

TABLE 8-continued

| Primer set | UP | | Primer set | NG | |
| | $C_T$ | $\Delta C_T$ | | $C_T$ | $\Delta C_T$ |
|---|---|---|---|---|---|
| Primer set #9B (UBP; $3^{rd}$) | 34.34 | 4.36 | Primer set #19B (UBP; $3^{rd}$) | 38.41 | 9.32 |
| Primer set #9C (UBP; $4^{th}$) | 47.22 | 17.24 | Primer set #19C (UBP; $4^{th}$) | 34.51 | 5.42 |
| Primer set #9D (UBP; $5^{th}$) | N/A | N/A | Primer set #19D (UBP; $5^{th}$) | N/A | N/A |
| Primer set #9E (UBP; $6^{th}$) | N/A | N/A | Primer set #19E (UBP; $6^{th}$) | N/A | N/A |
| Primer set #9F (UBP; $7^{th}$) | 30.70 | 0.72 | Primer set #19F (UBP; $7^{th}$) | 26.55 | −2.54 |
| Primer set #9G (UBP; $8^{th}$) | 29.86 | −0.12 | Primer set #19G (UBP; $8^{th}$) | 28.06 | −1.03 |

(N/A: not applicable)
(The number in parentheses refers to the position of deoxyinosine within the primer)

As shown in Table 8, dimer amplification was inhibited with the primer sets #9A-9E and #19A-19E (comprising UBPs with deoxyinosines at $2^{nd}$, $3^{rd}$, $4^{th}$, $5^{th}$ and $6^{th}$ positions); however, it was not inhibited with the primer sets #9F, #9G, #19F and #19G (comprising UBPs with deoxyinosines at $7^{th}$ and $8^{th}$ positions).

This result demonstrates that the UBP containing deoxyinosine at $2^{nd}$ to $6^{th}$ positions at its 3'-end is effective in preventing dimer amplification.

<2-2> Effects of UBPs with Deoxyinosines at Various Positions on Target Amplification In this Example, the effects of UBPs with universal bases at various positions on the target amplification were compared with that of conventional primers.

For this experiment, two conventional primers for amplifying a target nucleic acid molecule (Primer set #29 for UP or Primer set #39 for NG) and one primer for forming both-strands extendable primer dimers were first prepared. Then, one of the two conventional primers for amplifying a target nucleic acid molecule was modified to prepare various UBPs. The UBPs were prepared to contain deoxyinosines at various positions as in Example <2-1>.

Consequently, a conventional primer and a UBP for amplifying a target nucleic acid molecule were combined with a primer for forming both-strands extendable primer dimers to obtain various primer sets.

TaqMan real-time probes (SEQ ID NOs: 25 and 26) were further used for detection of amplification.

The primer sets used herein are provided in Table 9 below.

TABLE 9

| Primer set | Primer name | Sequence | SEQ ID NO |
|---|---|---|---|
| Primer set #29 (Conventional) | UP-F1 | 5'-GCACAATTTGGATCATTAAAAGGT-3' | 23 |
| | UP-R1 | 5'-GGTTCTCAAGCAACAATATCAGCT-3' | 1 |
| | UP-C-3 | 5'-TTGGCTTGGCTTGGCTT<u>AGCTGA</u>-3' | 10 |
| Primer set #29A (UBP) | UP-F1 | 5'-GCACAATTTGGATCATTAAAAGGT-3' | 23 |
| | UP-IR-2 | 5'-GGTTCTCAAGCAACAATATCAG<b>I</b>T-3' | 27 |
| | UP-C-3 | 5'-TTGGCTTGGCTTGGCTT<u>AGCTGA</u>-3' | 10 |
| Primer set #29B (UBP) | UP-F1 | 5'-GCACAATTTGGATCATTAAAAGGT-3' | 23 |
| | UP-IR-3 | 5'-GGTTCTCAAGCAACAATATCA<b>I</b>CT-3' | 28 |
| | UP-C-3 | 5'-TTGGCTTGGCTTGGCTT<u>AGCTGA</u>-3' | 10 |
| Primer set #29C (UBP) | UP-F1 | 5'-GCACAATTTGGATCATTAAAAGGT-3' | 23 |
| | UP-IR-4 | 5'-GGTTCTCAAGCAACAATATC<b>I</b>GCT-3' | 29 |
| | UP-C-3 | 5'-TTGGCTTGGCTTGGCTT<u>AGCTGA</u>-3' | 10 |

TABLE 9-continued

| Primer set | Primer name | Sequence | SEQ ID NO |
|---|---|---|---|
| Primer set #29D (UBP) | UP-F1 | 5'-GCACAATTTGGATCATTAAAAGGT-3' | 23 |
| | UP-IR-5 | 5'-GGTTCTCAAGCAACAATATIAGCT-3' | 30 |
| | UP-C-3 | 5'-TTGGCTTGGCTTGGCTTAGCTGA-3' | 10 |
| Primer set #29E (UBP) | UP-F1 | 5'-GCACAATTTGGATCATTAAAAGGT-3' | 23 |
| | UP-IR-6 | 5'-GGTTCTCAAGCAACAATAICAGCT-3' | 31 |
| | UP-C-3 | 5'-TTGGCTTGGCTTGGCTTAGCTGA-3' | 10 |
| Primer set #29F (UBP) | UP-F1 | 5'-GCACAATTTGGATCATTAAAAGGT-3' | 23 |
| | UP-IR-7 | 5'-GGTCTCAAGCAACAATITCAGCT-3' | 32 |
| | UP-C-3 | 5'-TTGGCTTGGCTTGGCTTAGCTGA-3' | 10 |
| Primer set #29G (UBP) | UP-F1 | 5'-GCACAATTTGGATCATTAAAAGGT-3' | 23 |
| | UP-IR-8 | 5'-GGTTCTCAAGCAACAAIATCAGCT-3' | 33 |
| | UP-C-3 | 5'-TTGGCTTGGCTTGGCTTAGCTGA-3' | 10 |
| Primer set #39 (Conventional) | NG-F4 | 5'-GCGGACAGTTGTTTTTCGACT-3' | 12 |
| | NG-R2 | 5'-GTCGTATCCGCATCCGTCAA-3' | 24 |
| | NG-C-3 | 5'-TTGGCTTGGCTTGGCTTAGTCGA-3' | 21 |
| Primer set #39A (UBP) | NG-IF-2 | 5'-GCGGACAGTTGTTTTTCGAIT-3' | 34 |
| | NG-R2 | 5'-GTCGTATCCGCATCCGTCAA-3' | 24 |
| | NG-C-3 | 5'-TTGGCTTGGCTTGGCTTAGTCGA-3' | 21 |
| Primer set #39B (UBP) | NG-IF-3 | 5'-GCGGACAGTTGTTTTTCGICT-3' | 35 |
| | NG-R2 | 5'-GTCGTATCCGCATCCGTCAA-3' | 24 |
| | NG-C-3 | 5'-TTGGCTTGGCTTGGCTTAGTCGA-3' | 21 |
| Primer set #39C (UBP) | NG-IF-4 | 5'-GCGGACAGTTGTTTTTCIACT-3' | 36 |
| | NG-R2 | 5'-GTCGTATCCGCATCCGTCAA-3' | 24 |
| | NG-C-3 | 5'-TTGGCTTGGCTTGGCTTAGTCGA-3' | 21 |
| Primer set #39D (UBP) | NG-IF-5 | 5'-GCGGACAGTTGTTTTTIGACT-3' | 37 |
| | NG-R2 | 5'-GTCGTATCCGCATCCGTCAA-3' | 24 |
| | NG-C-3 | 5'-TTGGCTTGGCTTGGCTTAGTCGA-3' | 21 |
| Primer set #39E (UBP) | NG-IF-6 | 5'-GCGGACAGTTGTTTTICGACT-3' | 38 |
| | NG-R2 | 5'-GTCGTATCCGCATCCGTCAA-3' | 24 |
| | NG-C-3 | 5'-TTGGCTTGGCTTGGCTTAGTCGA-3' | 21 |
| Primer set #39F (UBP) | NG-IF-7 | 5'-GCGGACAGTTGTTTITCGACT-3' | 39 |
| | NG-R2 | 5'-GTCGTATCCGCATCCGTCAA-3' | 24 |
| | NG-C-3 | 5'-TTGGCTTGGCTTGGCTTAGTCGA-3' | 21 |
| Primer set #39G (UBP) | NG-IF-8 | 5'-GCGGACAGTTGTTITTCGACT-3' | 40 |
| | NG-R2 | 5'-GTCGTATCCGCATCCGTCAA-3' | 24 |
| | NG-C-3 | 5'-TTGGCTTGGCTTGGCTTAGTCGA-3' | 21 |

(Underlined letters in UP-C-3 indicate the complementary sequences to UP-R1; and Underlined letters in NG-C-3 indicate the complementary sequences to NG-F4)

Specifically, the real-time PCR was conducted in the final volume of 20 µl containing each primer set (3 pmole of a conventional forward primer UP-F1 (SEQ ID NO: 23) and 3 pmole of one of a conventional reverse primer UP-R1 (SEQ ID NO: 1) and UBPs (SEQ ID NO: 27-33) for UP-target amplification, and 10 pmole of a primer for forming both-strands extendable primer dimers (SEQ ID NO: 10); or 3 pmole of a conventional reverse primer NG-R2 (SEQ ID NO:14) and 3 pmole of one of a conventional forward primer NG-F4 (SEQ ID NO: 13) and UBPs (SEQ ID NOs: 34-40) for NG-target amplification, and 10 pmole of a primer for forming both-strands extendable primer dimers (SEQ ID NO: 21)), a target nucleic acid sequence (0.1 pg of UP or 0.1 pg of NG), and 5 µl of 4× Master Mix [final, 200 µM dNTPs, 2 mM MgCl$_2$, 2 U of Taq DNA polymerase]. The tubes containing the reaction mixture were placed in the real-time thermocycler (CFX96, Bio-Rad) for 5 min at 50° C., denatured for 15 min at 95° C. and subjected to 50 cycles of 10 sec at 95° C., 60 sec at 57° C., 10 sec at 72° C. The detection of signals was performed at 95° C. at each cycle For comparison, the real-time PCR was conducted with primer sets without a primer for forming both-strands extendable primer dimers (UP-C-3 (SEQ ID NO: 10) or NG-C-3 (SEQ ID NO: 21)).

Figure 6A:
FIG. 6A shows amplification curves for a target nucleic acid molecule, UP, obtained by using a primer set #29 ($1^{st}$ row, left), a primer set #29A ($1^{st}$ row, right), a primer set #29B ($2^{nd}$ row, left), a primer set #29C ($2^{nd}$ row, right), a primer set #29D ($3^{rd}$ row, left), a primer set #29E ($3^{rd}$ row, right), a primer set #29F ($4^{th}$ row, left), and a primer set #29G ($4^{th}$ row, right), respectively. For comparison, amplification curves were obtained with primer sets #29 and #29A-#29G without a primer for forming both-strands extendable primer dimers (UP-C-3). In the figures, the results for primer sets #29 and #29A-#29G are represented by "-○-"; the results for the primer sets without a primer for forming primer dimers (UP-C-3) are represented by "-X-".
Figure 6B:
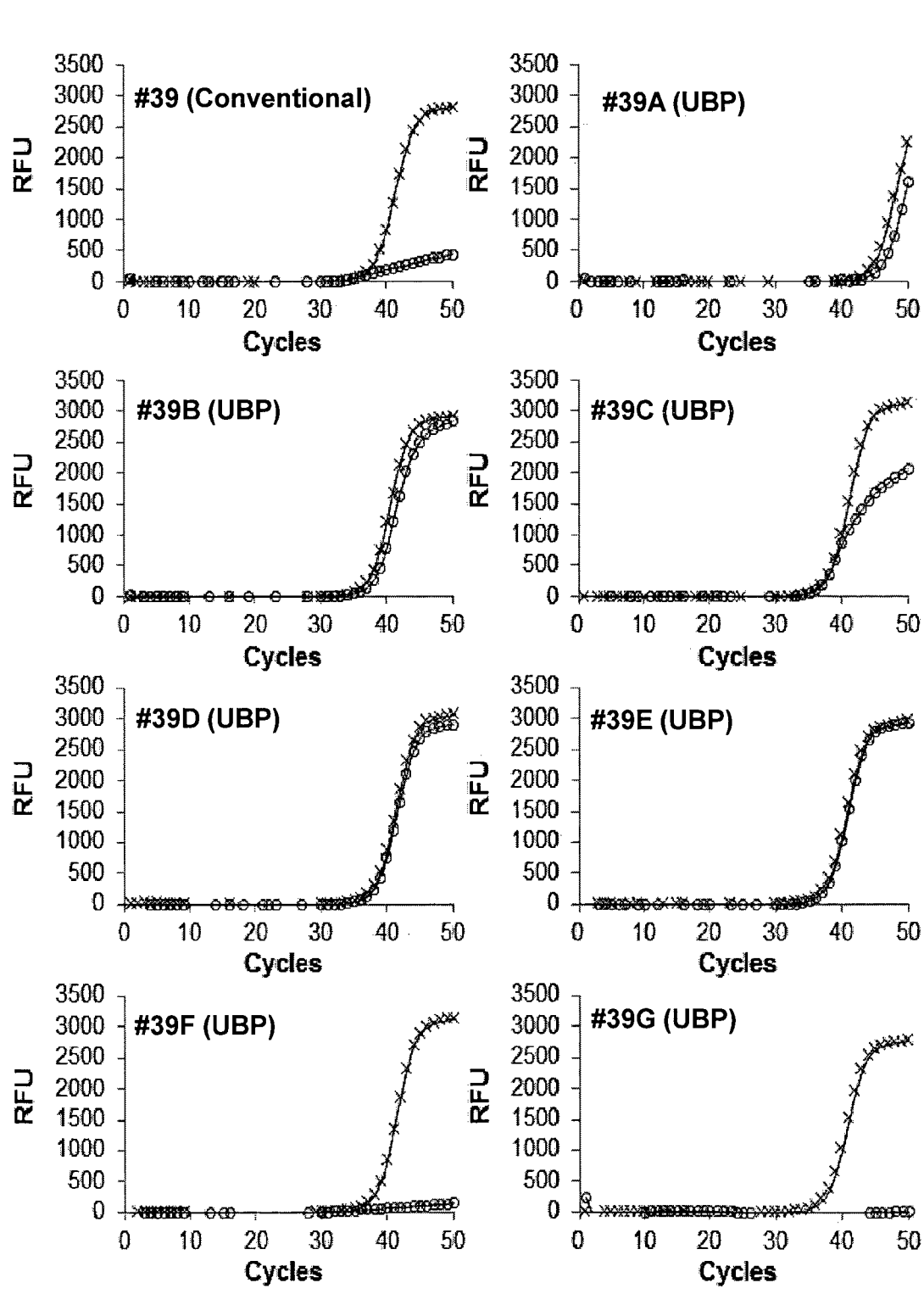
FIG. 6B shows amplification curves for a target nucleic acid molecule, NG, obtained by using a primer set #39 ($1^{st}$ row, left), a primer set #39A ($1^{st}$ row, right), a primer set #39B ($2^{nd}$ row, left), a primer set #39C ($2^{nd}$ row, right), a primer set #39D ($3^{rd}$ row, left), a primer set #39E ($3^{rd}$ row, right), a primer set #39F ($4^{th}$ row, left), and a primer set #39G ($4^{th}$ row, right), respectively. For comparison, amplification curves were obtained with primer sets #39 and #39A-#39G without a primer for forming both-strands extendable primer dimers (NG-C-3). In the figures, the results for primer sets #39 and #39A-#39G are represented by "-○-"; the results for the primer sets without a primer for forming primer dimers (NG-C-3) are represented by "-X-".

The amplification curves obtained from each primer set are shown in FIGS. 6A and 6B. In the figures, "-X-" represents the results for primer sets without a primer for forming primer dimers (UP-C-3 or NG-C-3); "-○-" represents the results for primer sets with a primer for forming primer dimers (UP-C-3 or NG-C-3). Threshold values, 150 and 400, were applied to calculate C$_T$ values of UP and NG, respectively, and then ΔC$_T$ values were calculated as below:

$$\Delta C_T = $$

[C$_T$ in a reaction in the presence of a primer for forming primer dimer] −

[C$_T$ in a reaction in the absence of a primer for forming primer dimer]

The $\Delta C_T$ values calculated are provided in Tables 10 and 11 below.

TABLE 10

| | UP | | |
| | $C_T$ | | |
| Primer set | Absence of UP-C-3 | Presence of UP-C-3 | $\Delta C_T$ |
|---|---|---|---|
| Primer set #29 (Conventional) | 38.55 | N/A | N/A |
| Primer set #29A (UBP; $2^{nd}$) | N/A | N/A | N/A |
| Primer set #29B (UBP; $3^{rd}$) | 37.6 | 38.3 | 0.7 |
| Primer set #29C (UBP; $4^{th}$) | 38.18 | 38.6 | 0.42 |
| Primer set #29D (UBP; $5^{th}$) | 38.62 | 38.64 | 0.02 |
| Primer set #29E (UBP; $6^{th}$) | 38.69 | 38.02 | -0.67 |
| Primer set #29F (UBP; $7^{th}$) | 38.87 | N/A | N/A |
| Primer set #29G (UBP; $8^{th}$) | 39.03 | N/A | N/A |

TABLE 11

| | NG | | |
| | $C_T$ | | |
| Primer set | Absence of NG-C-3 | Presence of NG-C-3 | $\Delta C_T$ |
|---|---|---|---|
| Primer set #39 (Conventional) | 38.55 | 48.43 | 9.88 |
| Primer set #39A (UBP; $2^{nd}$) | 45.3 | 46.7 | 1.4 |
| Primer set #39B (UBP; $3^{rd}$) | 37.79 | 38.7 | 0.91 |
| Primer set #39C (UBP; $4^{th}$) | 38.15 | 38.21 | 0.06 |
| Primer set #39D (UBP; $5^{th}$) | 38.52 | 38.8 | 0.28 |
| Primer set #39E (UBP; $6^{th}$) | 38.02 | 38.17 | 0.15 |
| Primer set #39F (UBP; $7^{th}$) | 38.59 | N/A | N/A |
| Primer set #39G (UBP; $8^{th}$) | 38.13 | N/A | N/A |

Detection of an amplification curve in the absence of a primer for forming primer dimers and $\Delta C_T$ value not more than 1.0 indicate that a target nucleic acid sequence is successfully amplified, irrespective of the presence of the primer for forming primer dimer.

As shown in Tables 10 and 11, primer sets #29 and #39 were able to amplify both UP and NG in the absence of a primer for forming primer dimer, but failed to amplify UP and NG in the presence of the primer for forming primer dimer.

Meanwhile, primer sets #29A and #39A (each comprising UBP with deoxyinosine at $2^{nd}$ position) failed to amplify UP and NG even in the absence of a primer for forming primer dimer; primer sets #29B-29E and 39B-39E (each comprising UBP with deoxyinosine at $3^{rd}$, $4^{th}$, $5^{th}$, or $6^{th}$ position) were able to amplify UP and NG in the presence or absence of a primer for forming primer dimer; primer sets #29F-29G and #39F-39G (each comprising UBP with deoxyinosine at $7^{th}$ or $8^{th}$ position succeeded to amplify UP and NG in the absence of a primer for forming primer dimer, but failed to amplify UP and NG in the presence of a primer for forming primer dimer The results demonstrate that UBPs with deoxyinosine between $3^{rd}$ to $6^{th}$ positions at their 3'-ends therein does not significantly affect target amplification.

Taken together, it will be appreciated that the use of UBP containing a universal base nucleotide at $3^{rd}$ to $6^{th}$ positions from the 3'-end therein can improve target amplification by inhibiting primer dimer formation.

Example 3: Verification of the Effect of UBP

We verified whether UBP of the present disclosure which contains a universal base at $3^{rd}$ to $6^{th}$ nucleotide from the 3'-end in a primer actually inhibit primer dimer formation in a multiplex amplification reaction.

<3-1> Utility of UBP on Reducing Primer Dimer Formation

For this experiment, three different types of primer mixtures were prepared as follows: (i) Conventional primer mixture; (ii) $1^{st}$ UBP mixture; and (iii) $2^{nd}$ UBP mixture.

Each of the primer mixtures (i)-(iii) consisted of four primer pairs for amplifying four target nucleic acid sequences, genomic DNAs of Ureaplasma urealyticum (UU), Mycoplasma genitalium (MG), Neisseria gonorrhoeae (NG), and Chlamydia trachomatis (CT), each primer pair comprising a forward primer and a reverse primer.

Specifically, the conventional primer mixture consisted of eight conventional primers containing no deoxyinosine in their sequences, which was used as a control. The $1^{st}$ UBP mixture consisted of four forward UBPs (containing one deoxyinosine) and four reverse conventional primers, and the $2^{nd}$ UBP mixture consisted of four forward UBPs (containing two deoxyinosines) and four reverse conventional primers. The UBPs were prepared by replacing one or two natural bases in a conventional primer with deoxyinosine.

The sequences of primers in the conventional primer mixture, $1^{st}$ UBP primer mixture, and $2^{nd}$ UBP primer mixture are provided in Table 12 below.

TABLE 12

| Type | Name | Sequence | SEQ ID NO |
|---|---|---|---|
| Conventional primer mixture | UU-F1 | 5'-GCATATGATGAAGCACACAACAAAATGG-3' | 41 |
| | UU-R1 | 5'-GCTTTGGCTGATGATTGCGTAG-3' | 42 |
| | MG-F1 | 5'-AAAACCCACGGAAATGATGAGA-3' | 43 |
| | MG-R1 | 5'-CTCGTTAATTTACCTATTCCATTTTG-3' | 44 |
| | NG-F1 | 5'-TACGCCTGCTACTTTCACGC-3' | 45 |
| | NG-R1 | 5'-CAATGGATCGGTATCACTCGC-3' | 46 |
| | CT-F1 | 5'-TTATTCATCCGAATGGATAAAGCGTGA-3' | 47 |
| | CT-R1 | 5'-AACAATGAATCCTGAGCAAAGG-3' | 48 |
| $1^{st}$ UBP mixture | UU-F2 | 5'-GCATATGATGAAGCACACAACAAAAIGG-3' | 49 |
| | UU-R1 | 5'-GCTTTGGCTGATGATTGCGTAG-3' | 42 |
| | MG-F2 | 5'-AAAACCCACGGAAATGAIGAGA-3' | 50 |
| | MG-R1 | 5'-CTCGTTAATTTACCTATTCCATTTTG-3' | 44 |
| | NG-F2 | 5'-TACGCCTGCTACTTTCICGC-3' | 51 |
| | NG-R1 | 5'-CAATGGATCGGTATCACTCGC-3' | 46 |
| | CT-F2 | 5'-TTATTCATCCGAATGGATAAAGCGIGA-3' | 52 |
| | CT-R1 | 5'-AACAATGAATCCTGAGCAAAGG-3' | 48 |
| $2^{nd}$ UBP mixture | UU-F3 | 5'-GCATATGATGAAICACACAACAAAAIGG-3' | 53 |

TABLE 12 -continued

| Type | Name | Sequence | SEQ ID NO |
|------|------|----------|-----------|
| | UU-R1 | 5'-GCTTTGGCTGATGATTGCGTAG-3' | 42 |
| | MG-F3 | 5'-AAAACCCACIGAAATGAIGAGA-3' | 54 |
| | MG-R1 | 5'-CTCGTTAATTTACCTATTCCATTTT G-3' | 44 |
| | NG-F3 | 5'-TACGCCTGCIACTTTCICGC-3' | 55 |
| | NG-R1 | 5'-CAATGGATCGGTATCACTCGC-3' | 46 |
| | CT-F3 | 5'-TTATTCATCCGAAIGGATAAAGCGI GA-3' | 56 |
| | CT-R1 | 5'-AACAATGAATCCTGAGCAAAGG-3' | 48 |

(I: Deoxyinosine)

Specifically, the real-time PCR was conducted in the final volume of 20 µl containing 3 pmole of each primer in the conventional primer mixture (SEQ ID NOs: 41-48), the 1$^{st}$ UBP mixture (SEQ ID Nos: 49, 42, 50, 44, 51, 46, 52 and 48) or the UBP mixture (SEQ ID Nos: 53, 42, 54, 44, 55, 46, 56 and 48), 2 µl of 10×SYBR® Green I, and 5 µl of 4× Master Mix [final, 200 µM dNTPs, 2 mM MgCl$_2$, 2 U of Taq DNA polymerase]. The tubes containing the reaction mixture were placed in the real-time thermocycler (CFX96, Bio-Rad) for 5 min at 50° C., denatured for 15 min at 95° C. and subjected to 50 cycles of 10 sec at 95° C., 60 sec at 57° C., 10 sec at 72° C. The detection of signals was performed at 57° C. at each cycle.

Figure 7:
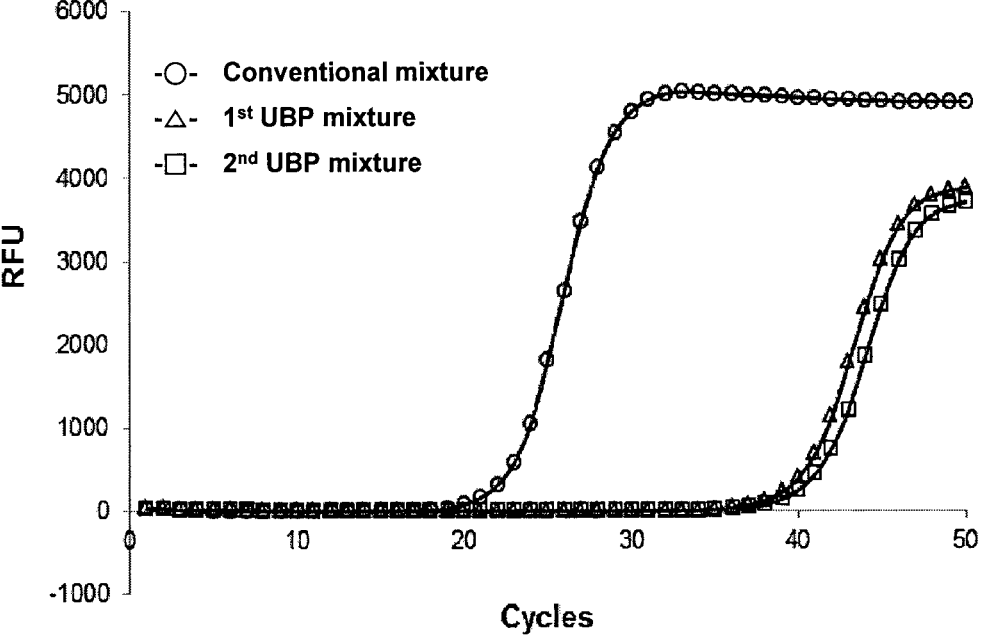
FIG. 7 shows amplification curves for primer dimers, obtained by using a conventional primer mixture (-○-), a $1^{st}$ UBP mixture (-Δ-) and a $2^{nd}$ UBP mixture (-□-).

The amplification curves obtained from the experiment above are shown in FIG. 7. Subsequently, in order to evaluate the degree of dimer amplification, a threshold value, 500, was employed to calculate cycle threshold (C$_T$) values.

As a result, the C$_T$ values for the 1$^{st}$ UBP mixture, and the 2$^{nd}$ UBP mixture (i.e., 40.36 and 41.2, respectively) were found to be higher than that for the conventional primer mixture (i.e., 22.71).

The results show that the use of the UBP of the present disclosure, particular containing a universal base at 3$^{rd}$ to 6$^{th}$ nucleotide from the 3'-end in a primer, can effectively inhibit dimer formation and amplification as compared to conventional primers, in a multiplex amplification reaction.

<3-2> Utility of UBP on Increasing Target Amplification

In this Example, TaqMan probes were applied to detect multiple target amplification as a signal generating mean.

The sequences of probes additionally used in this Example are provided in Table 13 below.

TABLE 13

| Name | Sequence | SEQ ID NO |
|------|----------|-----------|
| UU-P1 | 5'-[FAM]CACTTCACCAGATACATAACCCCCGCC [BHQ-1]-3' | 57 |
| MG-P1 | 5'-[CAL Fluor Orange 560]ACACCTCTTG CTGTTCTTGAAAGAACTC[BHQ-1]-3' | 58 |
| NG-P1 | 5'-[CAL Fluor Red 610]TGCCCCTCATTGG CGTGTTTCG[BHQ-2]-3' | 59 |
| CT-P1 | 5'-[Quasar 705]CATTGTAAAGATATGGTCTG CTTCGACCG[BHQ-3]-3' | 60 |

(BHQ: Black Hole Quencher)
(FAM, CAL Fluor Orange 560, CAL Fluor Red 610, and Quasar 705: fluorescent reporter molecules)

The real-time PCR was conducted in the final volume of 20 µl containing 3 pmole of each primer in the conventional mixture (SEQ ID NOs: 41-48), the 1$^{st}$ UBP mixture (SEQ ID Nos: 49, 42, 50, 44, 51, 46, 52 and 48) or the 2$^{nd}$ UBP mixture (SEQ ID Nos: 53, 42, 54, 44, 55, 46, 56 and 48), 3 pmole of TaqMan probes (SEQ ID NOs: 56-59), four target nucleic acid sequences (0 (NTC), 0.1, 1 or 10 pg of each genomic DNA), and 5 µl of 4× Master Mix [final, 200 µM dNTPs, 2 mM MgCl$_2$, 2 U of Taq DNA polymerase]. The tubes containing the reaction mixture were placed in the real-time thermocycler (CFX96, Bio-Rad) for 5 min at 50° C., denatured for 15 min at 95° C. and subjected to 50 cycles of 10 sec at 95° C., 60 sec at 57° C., 10 sec at 72° C. The detection of signals was performed at 95° C. at each cycle.

Figure 8:
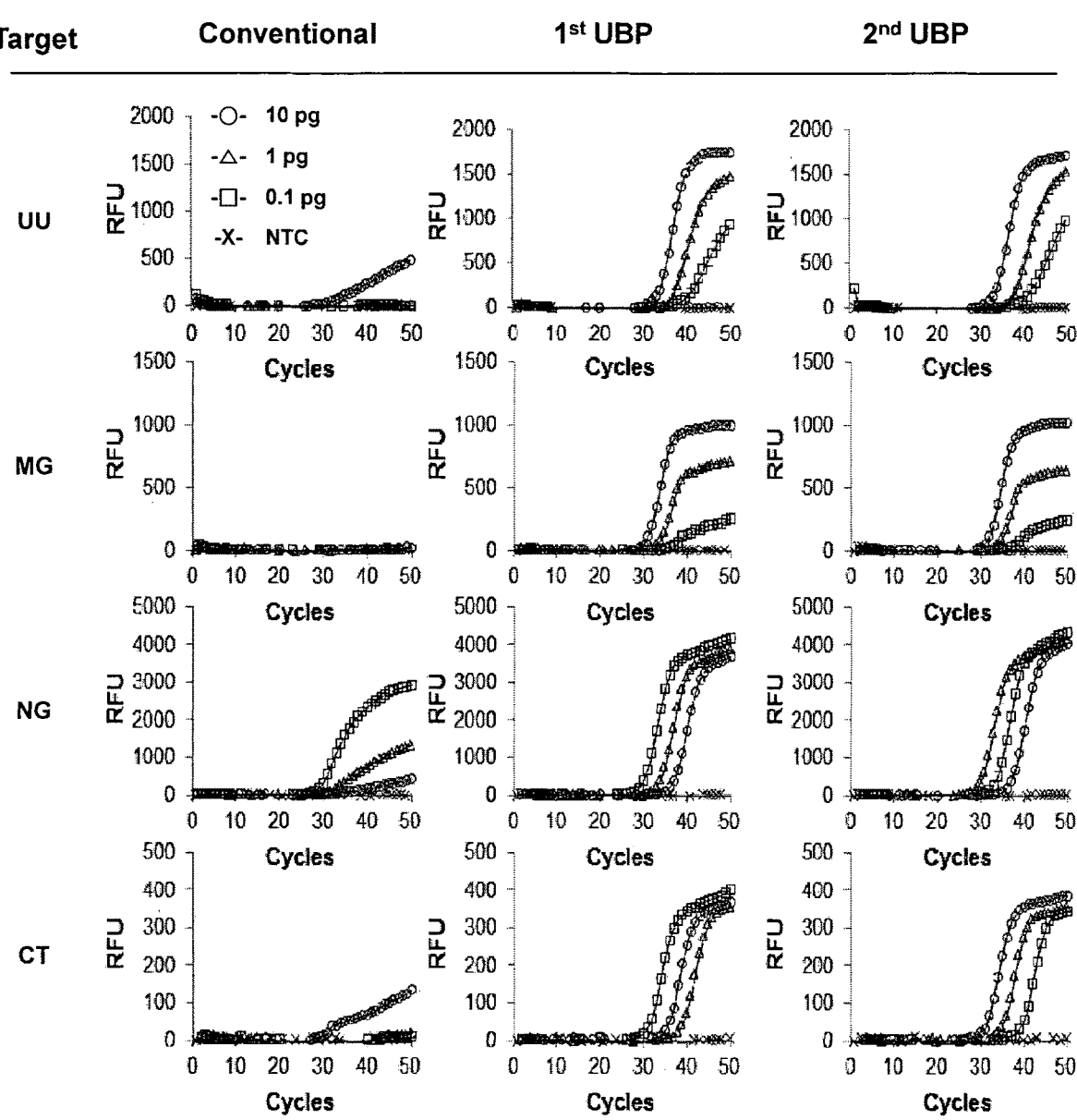
FIG. 8 shows amplification curves for target nucleic acid molecules, UU, MG, NG and CT, obtained by using a conventional primer mixture (left column), a $1^{st}$ UBP mixture (middle column) and a $2^{nd}$ UBP mixture (right column) in the presence of a target nucleic acid molecule at concentrations of 10 pg (-○-), 1 pg (-Δ-), 0.1 pg (-□-) and NTC (-X-).

The amplification curves obtained from the experiments above are shown in FIG. 8. As seen in FIG. 8, the conventional primer mixture was unable to amplify most of four target nucleic acid sequences at various concentrations. In contrast, both of the 1$^{st}$ UBP mixture and the 2$^{nd}$ UBP mixture were able to amplify all target nucleic acid sequences.

Then, in order to compare target amplification efficiency between the primer mixtures used, threshold values, 150, 100, 400, and 50, were applied to calculate C$_T$ values of UU, MG, NG, and CT, respectively.

The results are provided in Table 14 below.

TABLE 14

| | | C$_T$ | | |
|---|---|---|---|---|
| Target | | Conventional primer mixture | 1$^{st}$ UBP mixture | 2$^{nd}$ UBP mixture |
| UU | 10 pg | 37.01 | 33.35 | 33.2 |
| | 1 pg | N/A | 37.22 | 37.99 |
| | 0.1 pg | N/A | 40.58 | 41.18 |
| | NTC | N/A | N/A | N/A |
| MG | 10 pg | N/A | 30.75 | 31.76 |
| | 1 pg | N/A | 34.2 | 35.02 |
| | 0.1 pg | N/A | 38.74 | 39.53 |
| | NTC | N/A | N/A | N/A |
| NG | 10 pg | 30.37 | 30.09 | 30.13 |
| | 1 pg | 35.74 | 33.89 | 33.53 |
| | 0.1 pg | 49.48 | 37.04 | 37.11 |
| | NTC | N/A | N/A | N/A |
| CT | 10 pg | 34.81 | 31.57 | 31.55 |
| | 1 pg | N/A | 35.86 | 35.41 |
| | 0.1 pg | N/A | 39.19 | 39.84 |
| | NTC | N/A | N/A | N/A |

N/A: not applicable
NTC: no template control

As shown in Table 14, the conventional primer mixture could significantly amplify a few target nucleic acid sequences, i.e., 10 pg of UU, 10 pg, 1 pg and 0.1 pg of NG, and 10 pg of CT, among twelve target nucleic acid sequences at various concentrations. In contrast, the $1^{st}$ UBP mixture and the $2^{nd}$ UBP mixture, each containing UBPs of the present disclosure, could significantly amplify all twelve target nucleic acid sequences.

To further evaluate the effect of the method of the present invention on target amplification efficiency, amplification efficiency was calculated using a conventional program, LinRegPCR for the analysis of quantitative RT-PCR (qPCR) data (version 2017.1).

The program calculates the amplification efficiency using the input raw data and outputs it (the output amplification efficiency may be converted on a percent basis). In this example, the amplification efficiencies for the respective reactions using one of the conventional primer mixture, the $1^{st}$ UBP mixture and the $2^{nd}$ UBP mixture were obtained by the above program, and then the increase rate of efficiency for the $1^{st}$ UBP mixture or the $2^{nd}$ UBP mixture was calculated as follows:

$$\text{Increase rate of efficiency (\%) =} \quad \text{Equation 2}$$
$$[(\text{efficiency for an reaction using UBP/efficiency}$$
$$\text{for a reaction using conventional primers}) - 1] * 100$$

The results are provided in Table 15 below.

TABLE 15

| Template | | Efficiency (%) | | | Increase rate (%) | | |
| --- | --- | --- | --- | --- | --- | --- | --- |
| | | Conventional Primer mixture | $1^{st}$ UBP mixture | $2^{nd}$ UBP mixture | Conventional Primer mixture | $1^{st}$ UBP mixture | $2^{nd}$ UBP mixture |
| UU | 10 pg | 60.7% (1.214) | 87.0% (1.739) | 86.1% (1.721) | 0% | +43.2% | +41.8% |
| | 1 pg | N/A | 106.5% (2.129) | 90.6% (1.812) | 0% | >>100% | >>100% |
| | 0.1 pg | N/A | 74.8% (1.495) | 64.6% (1.292) | 0% | >>100% | >>100% |
| | NTC | N/A | N/A | N/A | 0% | N/A | N/A |
| MG | 10 pg | N/A | 82.7% (1.653) | 83.5% (1.670) | 0% | >>100% | >>100% |
| | 1 pg | N/A | 86.3% (1.726) | 86.5% (1.729) | 0% | >>100% | >>100% |
| | 0.1 pg | N/A | 75.3% (1.505) | 70.4% (1.407) | 0% | >>100% | >>100% |
| | NTC | N/A | N/A | N/A | 0% | N/A | N/A |
| NG | 10 pg | 101.5% (2.030) | 104.8% (2.096) | 110.5% (2.210) | 0% | +3.3% | +8.9% |
| | 1 pg | 78.1% (1.561) | 98.7% (1.974) | 97.8% (1.956) | 0% | +26.5% | +25.3% |
| | 0.1 pg | 59.3% (1.185) | 90.9% (1.817) | 94.8% (1.895) | 0% | +53.3% | +59.9% |
| | NTC | N/A | N/A | N/A | 0% | N/A | N/A |
| CT | 10 pg | 81.8% (1.635) | 91.4% (1.828) | 92.5% (1.850*) | 0% | +11.8% | +13.1% |
| | 1 pg | N/A | 85.5% (1.709) | 87.0% (1.740) | 0% | >>100% | >>100% |
| | 0.1 pg | N/A | 71.1% (1.422) | 98.5% (1.969) | 0% | >>100% | >>100% |
| | NTC | N/A | N/A | N/A | 0% | N/A | N/A |

As shown in Table 15, some of the reactions using the 1$^{st}$ UBP mixture and 2$^{nd}$ UBP mixture showed marked increase rates of efficiency compared to those using the conventional primer mixture (indicated as ">>100%" in the "increase rate" column), because the amplification efficiencies were not determined for the reactions using the conventional primer mixture but were determined for the reactions using the 1$^{st}$ UBP mixture and 2$^{nd}$ UBP mixture.

Further, some of the reactions using the 1$^{st}$ UBP mixture and 2$^{nd}$ UBP mixture showed increase rates of efficiency of 3.3%-59.9% compared to those using the conventional primer mixture.

The results show that the use of the UBP of the present disclosure, particular containing a universal base at 3$^{rd}$ to 6$^{th}$ nucleotide from the 3'-end in a primer, can improve target amplification efficiency as compared to the conventional primers, in a multiplex amplification reaction.

Having described a preferred embodiment of the present invention, it is to be understood that variants and modifications thereof falling within the spirit of the invention may become apparent to those skilled in this art, and the scope of this invention is to be determined by appended claims and their equivalents.

This application contains references to amino acid sequences and/or nucleic acid sequences which have been submitted herewith as the sequence listing text file. The aforementioned sequence listing is hereby incorporated by reference in its entirety pursuant to 37 C.F.R. 41.52(e).

---

What is claimed is:

1. A method for amplifying at least three target nucleic acid molecules with reduced primer dimer formation and determining the presence of them in a multiplex real-time amplification reaction, comprising the steps of:

(a) preparing at least three primer pairs and at least three probes, each primer pair comprising a forward primer and a reverse primer;

wherein each primer comprises a hybridizing nucleotide sequence to a corresponding target nucleic acid molecule;

wherein at least 50% of primers in said at least three primer pairs are universal base primers (UBPs);

wherein the primers in said at least three primer pairs are different from each other;

wherein the UBP has 1-3 universal base nucleotides;

wherein one or two of the universal base nucleotides are located in a core region ranging from $3^{rd}$ nucleotide to $6^{th}$ nucleotide at the 3'-end of the UBP, and the remainder is located in a region ranging from $4^{th}$ nucleotide at the 5'-end of the UBP to $7^{th}$ nucleotide at the 3'-end of the UBP such that a multiplex real-time amplification reaction using the at least three primer pairs generates amplification products of the target nucleic acid molecules with reduced primer dimer formation;

wherein the nucleotide sequence in the 5' direction from the core region comprises a hybridizing nucleotide sequence to the corresponding target nucleic acid molecule;

wherein when the UBP has 2 or 3 universal base nucleotides, the universal base nucleotides are non-consecutive in the UBP;

wherein each of the UBPs is at least 12 nucleotides in length; wherein each of the at least three probes comprises a hybridizing nucleotide sequence to the target nucleic acid molecule to be amplified and is located between the forward primer and the reverse primer; and (b) performing a multiplex real-time amplification reaction comprising at least two cycles of primer annealing, primer extension and denaturation by using the at least three primer pairs and the at least three probes; wherein the multiplex real-time amplification reaction generates amplification products of the target nucleic acid molecules with reduced primer dimer formation; and (c) determining the presence of the at least three target nucleic acid molecules by detecting the amplification products.

2. The method of claim 1, wherein the core region ranges from $3^{rd}$ nucleotide to $5^{th}$ nucleotide at the 3'-end of the UBP and the remainder is located in a region ranging from $4^{th}$ nucleotide at the 5'-end of the UBP to $6^{th}$ nucleotide at the 3'-end of the UBP.

3. The method of claim 1, wherein both of primers in the at least one primer pair are UBPs.

4. The method of claim 1, wherein either or both of primers in each primer pair are UBPs.

5. The method of claim 1, wherein at least one of the UBPs does not comprise a degenerate base.

6. The method of claim 1, wherein at least five primer pairs are used for amplifying at least five target nucleic acid molecules.

7. The method of claim 1, wherein the primer annealing in the multiplex real-time amplification reaction is performed at 50° C. or higher.

8. The method of claim 1, wherein the method exhibits a target amplification efficiency of at least 3% higher than that of using primer(s) containing naturally occurring nucleotides (A, C, G or T (U)) complementary to the target nucleic acid sequence instead of the at least one UBPs.

9. The method of claim 1, wherein a Ct value obtained from a reaction using a primer pair containing the UBP in the absence of a target nucleic acid molecule is increased by 1 or more, as compared with that using a primer pair consisting of conventional primers in the absence of a target nucleic acid molecule.

10. The method of claim 1, wherein the at least three probes do not have a universal base nucleotide.

11. The method of claim 1, wherein the universal base nucleotide is selected from the group consisting of deoxyinosine, inosine, 7-deaza-2'-deoxyinosine, 2-aza-2'-deoxyinosine, 2'-OMe inosine, 2'-F inosine, deoxy 3-nitropyrrole, 3-nitropyrrole, 2'-OMe 3-nitropyrrole, 2'-F 3-nitropyrrole, 1-(2'-deoxy-beta-D-ribofuranosyl)-3-nitropyrrole, deoxy 5-nitroindole, 5-nitroindole, 2'-OMe 5-nitroindole, 2'-F 5-nitroindole, deoxy 4-nitrobenzimidazole, 4-nitrobenzimidazole, deoxy 4-aminobenzimidazole, 4-aminobenzimidazole, deoxy nebularine, 2'-F nebularine, 2'-F 4-nitrobenzimidazole, PNA-5-introindole, PNA-nebularine, PNA-inosine, PNA-4-nitrobenzimidazole, PNA-3-nitropyrrole, morpholino-5-nitroindole, morpholino-nebularine, morpholino-inosine, morpholino-4-nitrobenzimidazole, morpholino-3-nitropyrrole, phosphoramidate-5-nitroindole, phosphoramidate-nebularine, phosphoramidate-inosine, phosphoramidate-4-nitrobenzimidazole, phosphoramidate-3-nitropyrrole, 2'-O-methoxyethyl inosine, 2'-O-methoxyethyl nebularine, 2'-O-methoxyethyl 5-nitroindole, 2'-O-methoxyethyl 4-nitrobenzimidazole, 2'-O-methoxyethyl 3-nitropyrrole, and combinations thereof.

12. A method for reducing primer dimer formation in a multiplex real-time amplification reaction for at least three target nucleic acid molecules, comprising the steps of:

(a) determining at least three target nucleic acid molecules to be amplified;

(b) determining nucleotide sequences of at least three primer pairs and at least three probes, each primer pair comprising a forward primer and a reverse primer;

wherein each primer comprises a hybridizing nucleotide sequence to a corresponding target nucleic acid molecule; wherein each of the at least three probes comprises a hybridizing nucleotide sequence to the target nucleic acid molecule to be amplified and is located between the forward primer and the reverse primer;

(c) replacing 1-3 nucleotides in at least 50% of primers in said at least three primer pairs with universal base nucleotides to prepare universal base primers (UBPs);

wherein the primers in said at least three primer pairs are different from each other;

wherein the replacement with the universal base nucleotides allows the inhibition of primer dimer formation;

wherein the UBP has 1-3 universal base nucleotides;

wherein one or two of the universal base nucleotides are located in a core region ranging from $3^{rd}$ nucleotide to $6^{th}$ nucleotide at the 3'-end of the UBP, and the remainder is located in a region ranging from $4^{th}$ nucleotide at the 5'-end of the UBP to $7^{th}$ nucleotide at the 3'-end of the UBP;

wherein the nucleotide sequence in the 5' direction from the core region comprises a hybridizing nucleotide sequence to the corresponding target nucleic acid molecule;

wherein when the UBP has 2 or 3 universal base nucleotides the universal base nucleotides are non-consecutive in the UBP; and wherein each of the UBPs is at least 12 nucleotides in length; and (d) performing a multiplex real-time amplification reaction comprising at least two cycles of primer annealing, primer extension and denaturation by using the at least three primer pairs and the at least three probes; wherein the multiplex real-time amplification reaction generates amplification products of the target nucleic acid molecules with reduced primer dimer formation; and (c) determining the presence of the at least three target nucleic acid molecules by detecting the amplification products.

13. The method of claim 12, wherein the core region ranges from $3^{rd}$ nucleotide to $5^{th}$ nucleotide at the 3'-end of the UBP.

14. The method of claim 12, wherein both of primers in the at least one primer pair are UBPs.

15. The method of claim 12, wherein either or both of primers in each primer pair are UBPs.

\* \* \* \* \*

SEQUENCE LISTING

```
<160> NUMBER OF SEQ ID NOS: 61

<210> SEQ ID NO 1
<211> LENGTH: 24
<212> TYPE: DNA
<213> ORGANISM: Artificial Sequence
<220> FEATURE:
<223> OTHER INFORMATION: Synthetic oligonucleotide: UP-R1

<400> SEQUENCE: 1
ggttctcaag caacaatatc agct                                           24

<210> SEQ ID NO 2
<211> LENGTH: 11
<212> TYPE: DNA
<213> ORGANISM: Artificial Sequence
<220> FEATURE:
<223> OTHER INFORMATION: Synthetic oligonucleotide: UP-N-1

<400> SEQUENCE: 2
agctgatatt g                                                         11

<210> SEQ ID NO 3
<211> LENGTH: 13
<212> TYPE: DNA
<213> ORGANISM: Artificial Sequence
<220> FEATURE:
<223> OTHER INFORMATION: Synthetic oligonucleotide: UP-N-2

<400> SEQUENCE: 3
agctgatatt gtt                                                       13

<210> SEQ ID NO 4
<211> LENGTH: 15
<212> TYPE: DNA
<213> ORGANISM: Artificial Sequence
<220> FEATURE:
<223> OTHER INFORMATION: Synthetic oligonucleotide: UP-N-3

<400> SEQUENCE: 4
agctgatatt gttgc                                                     15

<210> SEQ ID NO 5
<211> LENGTH: 22
<212> TYPE: DNA
<213> ORGANISM: Artificial Sequence
<220> FEATURE:
<223> OTHER INFORMATION: Synthetic oligonucleotide: UP-P-1

<400> SEQUENCE: 5
ttggcttggc ttggcttagc tg                                             22
```

-continued

```
<210> SEQ ID NO 6
<211> LENGTH: 24
<212> TYPE: DNA
<213> ORGANISM: Artificial Sequence
<220> FEATURE:
<223> OTHER INFORMATION: Synthetic oligonucleotide: UP-P-2

<400> SEQUENCE: 6
ttggcttggc ttggcttagc tgat                                              24

<210> SEQ ID NO 7
<211> LENGTH: 26
<212> TYPE: DNA
<213> ORGANISM: Artificial Sequence
<220> FEATURE:
<223> OTHER INFORMATION: Synthetic oligonucleotide: UP-P-3

<400> SEQUENCE: 7
ttggcttggc ttggcttagc tgatat                                            26

<210> SEQ ID NO 8
<211> LENGTH: 21
<212> TYPE: DNA
<213> ORGANISM: Artificial Sequence
<220> FEATURE:
<223> OTHER INFORMATION: Synthetic oligonucleotide: UP-C-1

<400> SEQUENCE: 8
ttggcttggc ttggcttagc t                                                 21

<210> SEQ ID NO 9
<211> LENGTH: 22
<212> TYPE: DNA
<213> ORGANISM: Artificial Sequence
<220> FEATURE:
<223> OTHER INFORMATION: Synthetic oligonucleotide: UP-C-2

<400> SEQUENCE: 9
ttggcttggc ttggcttagc tg                                                22

<210> SEQ ID NO 10
<211> LENGTH: 23
<212> TYPE: DNA
<213> ORGANISM: Artificial Sequence
<220> FEATURE:
<223> OTHER INFORMATION: Synthetic oligonucleotide: UP-C-3

<400> SEQUENCE: 10
ttggcttggc ttggcttagc tga                                               23

<210> SEQ ID NO 11
<211> LENGTH: 24
<212> TYPE: DNA
<213> ORGANISM: Artificial Sequence
<220> FEATURE:
<223> OTHER INFORMATION: Synthetic oligonucleotide: UP-C-4

<400> SEQUENCE: 11
ttggcttggc ttggcttagc tgat                                              24

<210> SEQ ID NO 12
<211> LENGTH: 21
<212> TYPE: DNA
<213> ORGANISM: Artificial Sequence
<220> FEATURE:
```

<223> OTHER INFORMATION: Synthetic oligonucleotide: NG-F4

<400> SEQUENCE: 12
gcggacagtt gttttttcgac t                                            21

<210> SEQ ID NO 13
<211> LENGTH: 11
<212> TYPE: DNA
<213> ORGANISM: Artificial Sequence
<220> FEATURE:
<223> OTHER INFORMATION: Synthetic oligonucleotide: NG-N-1

<400> SEQUENCE: 13
agtcgaaaaa c                                                        11

<210> SEQ ID NO 14
<211> LENGTH: 13
<212> TYPE: DNA
<213> ORGANISM: Artificial Sequence
<220> FEATURE:
<223> OTHER INFORMATION: Synthetic oligonucleotide: NG-N-2

<400> SEQUENCE: 14
agtcgaaaaa caa                                                      13

<210> SEQ ID NO 15
<211> LENGTH: 15
<212> TYPE: DNA
<213> ORGANISM: Artificial Sequence
<220> FEATURE:
<223> OTHER INFORMATION: Synthetic oligonucleotide: NG-N-3

<400> SEQUENCE: 15
agtcgaaaaa caact                                                    15

<210> SEQ ID NO 16
<211> LENGTH: 22
<212> TYPE: DNA
<213> ORGANISM: Artificial Sequence
<220> FEATURE:
<223> OTHER INFORMATION: Synthetic oligonucleotide: NG-P-1

<400> SEQUENCE: 16
ttggcttggc ttggcttagt cg                                            22

<210> SEQ ID NO 17
<211> LENGTH: 24
<212> TYPE: DNA
<213> ORGANISM: Artificial Sequence
<220> FEATURE:
<223> OTHER INFORMATION: Synthetic oligonucleotide: NG-P-2

<400> SEQUENCE: 17
ttggcttggc ttggcttagt cgaa                                          24

<210> SEQ ID NO 18
<211> LENGTH: 26
<212> TYPE: DNA
<213> ORGANISM: Artificial Sequence
<220> FEATURE:
<223> OTHER INFORMATION: Synthetic oligonucleotide: NG-P-3

<400> SEQUENCE: 18
ttggcttggc ttggcttagt cgaaaa                                        26

```
<210> SEQ ID NO 19
<211> LENGTH: 21
<212> TYPE: DNA
<213> ORGANISM: Artificial Sequence
<220> FEATURE:
<223> OTHER INFORMATION: Synthetic oligonucleotide: NG-C-1

<400> SEQUENCE: 19
ttggcttggc ttggcttagt c                                        21

<210> SEQ ID NO 20
<211> LENGTH: 22
<212> TYPE: DNA
<213> ORGANISM: Artificial Sequence
<220> FEATURE:
<223> OTHER INFORMATION: Synthetic oligonucleotide: NG-C-2

<400> SEQUENCE: 20
ttggcttggc ttggcttagt cg                                       22

<210> SEQ ID NO 21
<211> LENGTH: 23
<212> TYPE: DNA
<213> ORGANISM: Artificial Sequence
<220> FEATURE:
<223> OTHER INFORMATION: Synthetic oligonucleotide: NG-C-3

<400> SEQUENCE: 21
ttggcttggc ttggcttagt cga                                      23

<210> SEQ ID NO 22
<211> LENGTH: 24
<212> TYPE: DNA
<213> ORGANISM: Artificial Sequence
<220> FEATURE:
<223> OTHER INFORMATION: Synthetic oligonucleotide: NG-C-4

<400> SEQUENCE: 22
ttggcttggc ttggcttagt cgaa                                     24

<210> SEQ ID NO 23
<211> LENGTH: 24
<212> TYPE: DNA
<213> ORGANISM: Artificial Sequence
<220> FEATURE:
<223> OTHER INFORMATION: Synthetic oligonucleotide: UP-F1

<400> SEQUENCE: 23
gcacaatttg gatcattaaa aggt                                     24

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide: NG-R2

<400> SEQUENCE: 24
gtcgtatccg catccgtcaa                                          20

<210> SEQ ID NO 25
<211> LENGTH: 25
<212> TYPE: DNA
<213> ORGANISM: Artificial Sequence
<220> FEATURE:
<223> OTHER INFORMATION: Synthetic oligonucleotide: UP-P1
```

-continued

```
<400> SEQUENCE: 25
cccagctatt gcacatggtg ttgat                                          25

<210> SEQ ID NO 26
<211> LENGTH: 22
<212> TYPE: DNA
<213> ORGANISM: Artificial Sequence
<220> FEATURE:
<223> OTHER INFORMATION: Synthetic oligonucleotide: NG-P2

<400> SEQUENCE: 26
tgtacggctc cgttgtggcg gt                                             22

<210> SEQ ID NO 27
<211> LENGTH: 24
<212> TYPE: DNA
<213> ORGANISM: Artificial Sequence
<220> FEATURE:
<223> OTHER INFORMATION: Synthetic oligonucleotide: UP-IR-2
<220> FEATURE:
<221> NAME/KEY: misc_feature
<222> LOCATION: (23)..(23)
<223> OTHER INFORMATION: n is deoxyinosine

<400> SEQUENCE: 27
ggttctcaag caacaatatc agnt                                           24

<210> SEQ ID NO 28
<211> LENGTH: 24
<212> TYPE: DNA
<213> ORGANISM: Artificial Sequence
<220> FEATURE:
<223> OTHER INFORMATION: Synthetic oligonucleotide: UP-IR-3
<220> FEATURE:
<221> NAME/KEY: misc_feature
<222> LOCATION: (22)..(22)
<223> OTHER INFORMATION: n is deoxyinosine

<400> SEQUENCE: 28
ggttctcaag caacaatatc anct                                           24

<210> SEQ ID NO 29
<211> LENGTH: 24
<212> TYPE: DNA
<213> ORGANISM: Artificial Sequence
<220> FEATURE:
<223> OTHER INFORMATION: Synthetic oligonucleotide: UP-IR-4
<220> FEATURE:
<221> NAME/KEY: misc_feature
<222> LOCATION: (21)..(21)
<223> OTHER INFORMATION: n is deoxyinosine

<400> SEQUENCE: 29
ggttctcaag caacaatatc ngct                                           24

<210> SEQ ID NO 30
<211> LENGTH: 24
<212> TYPE: DNA
<213> ORGANISM: Artificial Sequence
<220> FEATURE:
<223> OTHER INFORMATION: Synthetic oligonucleotide: UP-IR-5
<220> FEATURE:
<221> NAME/KEY: misc_feature
<222> LOCATION: (20)..(20)
<223> OTHER INFORMATION: n is deoxyinosine

<400> SEQUENCE: 30
ggttctcaag caacaatatn agct                                           24
```

```
<210> SEQ ID NO 31
<211> LENGTH: 24
<212> TYPE: DNA
<213> ORGANISM: Artificial Sequence
<220> FEATURE:
<223> OTHER INFORMATION: Synthetic oligonucleotide: UP-IR-6
<220> FEATURE:
<221> NAME/KEY: misc_feature
<222> LOCATION: (19)..(19)
<223> OTHER INFORMATION: n is deoxyinosine

<400> SEQUENCE: 31
ggttctcaag caacaatanc agct                                              24

<210> SEQ ID NO 32
<211> LENGTH: 24
<212> TYPE: DNA
<213> ORGANISM: Artificial Sequence
<220> FEATURE:
<223> OTHER INFORMATION: Synthetic oligonucleotide: UP-IR-7
<220> FEATURE:
<221> NAME/KEY: misc_feature
<222> LOCATION: (18)..(18)
<223> OTHER INFORMATION: n is deoxyinosine

<400> SEQUENCE: 32
ggttctcaag caacaatntc agct                                              24

<210> SEQ ID NO 33
<211> LENGTH: 24
<212> TYPE: DNA
<213> ORGANISM: Artificial Sequence
<220> FEATURE:
<223> OTHER INFORMATION: Synthetic oligonucleotide: UP-IR-8
<220> FEATURE:
<221> NAME/KEY: misc_feature
<222> LOCATION: (17)..(17)
<223> OTHER INFORMATION: n is deoxyinosine

<400> SEQUENCE: 33
ggttctcaag caacaanatc agct                                              24

<210> SEQ ID NO 34
<211> LENGTH: 21
<212> TYPE: DNA
<213> ORGANISM: Artificial Sequence
<220> FEATURE:
<223> OTHER INFORMATION: Synthetic oligonucleotide: NG-IF-2
<220> FEATURE:
<221> NAME/KEY: misc_feature
<222> LOCATION: (20)..(20)
<223> OTHER INFORMATION: n is deoxyinosine

<400> SEQUENCE: 34
gcggacagtt gtttttcgan t                                                 21

<210> SEQ ID NO 35
<211> LENGTH: 21
<212> TYPE: DNA
<213> ORGANISM: Artificial Sequence
<220> FEATURE:
<223> OTHER INFORMATION: Synthetic oligonucleotide: NG-IF-3
<220> FEATURE:
<221> NAME/KEY: misc_feature
<222> LOCATION: (19)..(19)
<223> OTHER INFORMATION: n is deoxyinosine

<400> SEQUENCE: 35
```

-continued

```
gcggacagtt gttttttcgnc t                                      21

<210> SEQ ID NO 36
<211> LENGTH: 21
<212> TYPE: DNA
<213> ORGANISM: Artificial Sequence
<220> FEATURE:
<223> OTHER INFORMATION: Synthetic oligonucleotide: NG-IF-4
<220> FEATURE:
<221> NAME/KEY: misc_feature
<222> LOCATION: (18)..(18)
<223> OTHER INFORMATION: n is deoxyinosine

<400> SEQUENCE: 36
gcggacagtt gttttttcnac t                                      21

<210> SEQ ID NO 37
<211> LENGTH: 21
<212> TYPE: DNA
<213> ORGANISM: Artificial Sequence
<220> FEATURE:
<223> OTHER INFORMATION: Synthetic oligonucleotide: NG-IF-5
<220> FEATURE:
<221> NAME/KEY: misc_feature
<222> LOCATION: (17)..(17)
<223> OTHER INFORMATION: n is deoxyinosine

<400> SEQUENCE: 37
gcggacagtt gtttttngac t                                       21

<210> SEQ ID NO 38
<211> LENGTH: 21
<212> TYPE: DNA
<213> ORGANISM: Artificial Sequence
<220> FEATURE:
<223> OTHER INFORMATION: Synthetic oligonucleotide: NG-IF-6
<220> FEATURE:
<221> NAME/KEY: misc_feature
<222> LOCATION: (16)..(16)
<223> OTHER INFORMATION: n is deoxyinosine

<400> SEQUENCE: 38
gcggacagtt gttttncgac t                                       21

<210> SEQ ID NO 39
<211> LENGTH: 21
<212> TYPE: DNA
<213> ORGANISM: Artificial Sequence
<220> FEATURE:
<223> OTHER INFORMATION: Synthetic oligonucleotide: NG-IF-7
<220> FEATURE:
<221> NAME/KEY: misc_feature
<222> LOCATION: (15)..(15)
<223> OTHER INFORMATION: n is deoxyinosine

<400> SEQUENCE: 39
gcggacagtt gtttntcgac t                                       21

<210> SEQ ID NO 40
<211> LENGTH: 21
<212> TYPE: DNA
<213> ORGANISM: Artificial Sequence
<220> FEATURE:
<223> OTHER INFORMATION: Synthetic oligonucleotide: NG-IF-8
<220> FEATURE:
<221> NAME/KEY: misc_feature
<222> LOCATION: (14)..(14)
<223> OTHER INFORMATION: n is deoxyinosine

<400> SEQUENCE: 40
```

```
gcggacagtt gttnttcgac t                                    21

<210> SEQ ID NO 41
<211> LENGTH: 28
<212> TYPE: DNA
<213> ORGANISM: Artificial Sequence
<220> FEATURE:
<223> OTHER INFORMATION: Synthetic oligonucleotide: UU-F1

<400> SEQUENCE: 41
gcatatgatg aagcacacaa caaaatgg                              28

<210> SEQ ID NO 42
<211> LENGTH: 22
<212> TYPE: DNA
<213> ORGANISM: Artificial Sequence
<220> FEATURE:
<223> OTHER INFORMATION: Synthetic oligonucleotide: UU-R1

<400> SEQUENCE: 42
gctttggctg atgattgcgt ag                                   22

<210> SEQ ID NO 43
<211> LENGTH: 22
<212> TYPE: DNA
<213> ORGANISM: Artificial Sequence
<220> FEATURE:
<223> OTHER INFORMATION: Synthetic oligonucleotide: MG-F1

<400> SEQUENCE: 43
aaaacccacg gaaatgatga ga                                   22

<210> SEQ ID NO 44
<211> LENGTH: 26
<212> TYPE: DNA
<213> ORGANISM: Artificial Sequence
<220> FEATURE:
<223> OTHER INFORMATION: Synthetic oligonucleotide: MG-R1

<400> SEQUENCE: 44
ctcgttaatt tacctattcc attttg                               26

<210> SEQ ID NO 45
<211> LENGTH: 20
<212> TYPE: DNA
<213> ORGANISM: Artificial Sequence
<220> FEATURE:
<223> OTHER INFORMATION: Synthetic oligonucleotide: NG-F1

<400> SEQUENCE: 45
tacgcctgct actttcacgc                                      20

<210> SEQ ID NO 46
<211> LENGTH: 21
<212> TYPE: DNA
<213> ORGANISM: Artificial Sequence
<220> FEATURE:
<223> OTHER INFORMATION: Synthetic oligonucleotide: NG-R1

<400> SEQUENCE: 46
caatggatcg gtatcactcg c                                    21

<210> SEQ ID NO 47
<211> LENGTH: 27
<212> TYPE: DNA
```

<213> ORGANISM: Artificial Sequence
<220> FEATURE:
<223> OTHER INFORMATION: Synthetic oligonucleotide: CT-F1

<400> SEQUENCE: 47
ttattcatcc gaatggataa agcgtga                                      27

<210> SEQ ID NO 48
<211> LENGTH: 22
<212> TYPE: DNA
<213> ORGANISM: Artificial Sequence
<220> FEATURE:
<223> OTHER INFORMATION: Synthetic oligonucleotide: CT-R1

<400> SEQUENCE: 48
aacaatgaat cctgagcaaa gg                                           22

<210> SEQ ID NO 49
<211> LENGTH: 28
<212> TYPE: DNA
<213> ORGANISM: Artificial Sequence
<220> FEATURE:
<223> OTHER INFORMATION: Synthetic oligonucleotide: UU-F2
<220> FEATURE:
<221> NAME/KEY: misc_feature
<222> LOCATION: (26)..(26)
<223> OTHER INFORMATION: n is deoxyinosine

<400> SEQUENCE: 49
gcatatgatg aagcacacaa caaaangg                                     28

<210> SEQ ID NO 50
<211> LENGTH: 22
<212> TYPE: DNA
<213> ORGANISM: Artificial Sequence
<220> FEATURE:
<223> OTHER INFORMATION: Synthetic oligonucleotide: MG-F2
<220> FEATURE:
<221> NAME/KEY: misc_feature
<222> LOCATION: (18)..(18)
<223> OTHER INFORMATION: n is deoxyinosine

<400> SEQUENCE: 50
aaaacccacg gaaatganga ga                                           22

<210> SEQ ID NO 51
<211> LENGTH: 20
<212> TYPE: DNA
<213> ORGANISM: Artificial Sequence
<220> FEATURE:
<223> OTHER INFORMATION: Synthetic oligonucleotide: NG-F2
<220> FEATURE:
<221> NAME/KEY: misc_feature
<222> LOCATION: (17)..(17)
<223> OTHER INFORMATION: n is deoxyinosine

<400> SEQUENCE: 51
tacgcctgct actttcncgc                                             20

<210> SEQ ID NO 52
<211> LENGTH: 27
<212> TYPE: DNA
<213> ORGANISM: Artificial Sequence
<220> FEATURE:
<223> OTHER INFORMATION: Synthetic oligonucleotide: CT-F2
<220> FEATURE:
<221> NAME/KEY: misc_feature
<222> LOCATION: (25)..(25)
<223> OTHER INFORMATION: n is deoxyinosine -continued

<400> SEQUENCE: 52
ttattcatcc gaatggataa agcgnga                                        27

<210> SEQ ID NO 53
<211> LENGTH: 28
<212> TYPE: DNA
<213> ORGANISM: Artificial Sequence
<220> FEATURE:
<223> OTHER INFORMATION: Synthetic oligonucleotide: UU-F3
<220> FEATURE:
<221> NAME/KEY: misc_feature
<222> LOCATION: (13)..(13)
<223> OTHER INFORMATION: n is deoxyinosine
<220> FEATURE:
<221> NAME/KEY: misc_feature
<222> LOCATION: (26)..(26)
<223> OTHER INFORMATION: n is deoxyinosine

<400> SEQUENCE: 53
gcatatgatg aancacacaa caaaangg                                       28

<210> SEQ ID NO 54
<211> LENGTH: 22
<212> TYPE: DNA
<213> ORGANISM: Artificial Sequence
<220> FEATURE:
<223> OTHER INFORMATION: Synthetic oligonucleotide: MG-F3
<220> FEATURE:
<221> NAME/KEY: misc_feature
<222> LOCATION: (10)..(10)
<223> OTHER INFORMATION: n is deoxyinosine
<220> FEATURE:
<221> NAME/KEY: misc_feature
<222> LOCATION: (18)..(18)
<223> OTHER INFORMATION: n is deoxyinosine

<400> SEQUENCE: 54
aaaacccacn gaaatganga ga                                             22

<210> SEQ ID NO 55
<211> LENGTH: 20
<212> TYPE: DNA
<213> ORGANISM: Artificial Sequence
<220> FEATURE:
<223> OTHER INFORMATION: Synthetic oligonucleotide: NG-F3
<220> FEATURE:
<221> NAME/KEY: misc_feature
<222> LOCATION: (10)..(10)
<223> OTHER INFORMATION: n is deoxyinosine
<220> FEATURE:
<221> NAME/KEY: misc_feature
<222> LOCATION: (17)..(17)
<223> OTHER INFORMATION: n is deoxyinosine

<400> SEQUENCE: 55
tacgcctgcn actttcncgc                                                20

<210> SEQ ID NO 56
<211> LENGTH: 27
<212> TYPE: DNA
<213> ORGANISM: Artificial Sequence
<220> FEATURE:
<223> OTHER INFORMATION: Synthetic oligonucleotide: CT-F3
<220> FEATURE:
<221> NAME/KEY: misc_feature
<222> LOCATION: (14)..(14)
<223> OTHER INFORMATION: n is deoxyinosine
<220> FEATURE:
<221> NAME/KEY: misc_feature
<222> LOCATION: (25)..(25)

-continued

<223> OTHER INFORMATION: n is deoxyinosine

<400> SEQUENCE: 56
ttattcatcc gaanggataa agcgnga                                              27

<210> SEQ ID NO 57
<211> LENGTH: 27
<212> TYPE: DNA
<213> ORGANISM: Artificial Sequence
<220> FEATURE:
<223> OTHER INFORMATION: Synthetic oligonucleotide: UU-P1

<400> SEQUENCE: 57
cacttcacca gatacataac ccccgcc                                             27

<210> SEQ ID NO 58
<211> LENGTH: 28
<212> TYPE: DNA
<213> ORGANISM: Artificial Sequence
<220> FEATURE:
<223> OTHER INFORMATION: Synthetic oligonucleotide: MG-P1

<400> SEQUENCE: 58
acacctcttg ctgttcttga aagaactc                                            28

<210> SEQ ID NO 59
<211> LENGTH: 22
<212> TYPE: DNA
<213> ORGANISM: Artificial Sequence
<220> FEATURE:
<223> OTHER INFORMATION: Synthetic oligonucloetide: NG-P1

<400> SEQUENCE: 59
tgcccctcat tggcgtgttt cg                                                  22

<210> SEQ ID NO 60
<211> LENGTH: 29
<212> TYPE: DNA
<213> ORGANISM: Artificial Sequence
<220> FEATURE:
<223> OTHER INFORMATION: Synthetic oligonucleotide: CT-P1

<400> SEQUENCE: 60
cattgtaaag atatggtctg cttcgaccg                                           29

<210> SEQ ID NO 61
<211> LENGTH: 17
<212> TYPE: DNA
<213> ORGANISM: Artificial Sequence
<220> FEATURE:
<223> OTHER INFORMATION: Generic synthetic primer
<220> FEATURE:
<221> NAME/KEY: misc_feature
<222> LOCATION: (3)..(15)
<220> FEATURE:
<221> NAME/KEY: misc_feature
<222> LOCATION: (3)..(15)
<223> OTHER INFORMATION: N can be any nucleotide

<400> SEQUENCE: 61
agnnnnnnnn nnnnnct                                                        17